(12) United States Patent
Hebrink et al.

(10) Patent No.: US 11,940,651 B2
(45) Date of Patent: Mar. 26, 2024

(54) ULTRAVIOLET C LIGHT GUIDES

(71) Applicant: 3M INNOVATIVE PROPERTIES COMPANY, St. Paul, MN (US)

(72) Inventors: Timothy J. Hebrink, Scandia, MN (US); Stephen P. Maki, North St. Paul, MN (US); Michael E. Griffin, Maplewood, MN (US); Anna C. Hamlin, Lino Lakes, MN (US); Justin M. Mazzoni, Cheshire, CT (US); Christopher A. Merton, St. Louis Park, MN (US); Matthew T. Scholz, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 381 days.

(21) Appl. No.: 17/309,683

(22) PCT Filed: Dec. 23, 2019

(86) PCT No.: PCT/IB2019/061296
§ 371 (c)(1),
(2) Date: Jun. 15, 2021

(87) PCT Pub. No.: WO2020/136557
PCT Pub. Date: Jul. 2, 2020

(65) Prior Publication Data
US 2022/0026633 A1 Jan. 27, 2022

Related U.S. Application Data

(60) Provisional application No. 62/785,031, filed on Dec. 26, 2018.

(51) Int. Cl.
*G02B 6/10* (2006.01)
*A61L 2/10* (2006.01)
(Continued)

(52) U.S. Cl.
CPC .............. *G02B 6/102* (2013.01); *A61L 2/10* (2013.01); *A61L 2/26* (2013.01); *C02F 1/32* (2013.01);
(Continued)

(58) Field of Classification Search
None
See application file for complete search history.

(56) References Cited

U.S. PATENT DOCUMENTS 5,084,096 A 1/1992 Stovicek
5,408,022 A 4/1995 Imazato
(Continued)

FOREIGN PATENT DOCUMENTS

DE 102014105478 7/2015
WO WO1995-016754 6/1995
(Continued)

OTHER PUBLICATIONS

Block, Disinfection, Sterilization and Preservation, 225-255 (1991).
(Continued)

*Primary Examiner* — Rhonda S Peace
(74) *Attorney, Agent, or Firm* — Thomas M. Spielbauer; James A. Baker

(57) ABSTRACT

A light guide comprising a polymeric layer at least 25 percent transmissive over at least a 30 nm bandwidth in a wavelength range from 180 to 280 nm over a distance of at least 100 micrometers and visible light transparent reflecting layers (UV-C mirror) that are at least 50 percent reflective over at least 30 nm bandwidth in a wavelength range from 180 to 280 nm over an incident light angle of 0 to 90 degrees and that are at least 25 percent transmissive of visible light over at least 30 nm bandwidth in a wavelength range of 400
(Continued)

to 800 nm over an incident light angle of 0 to 90 degrees. The light guide is useful, for example, for antimicrobial surfaces.

15 Claims, 5 Drawing Sheets

(51) Int. Cl.
*A61L 2/26* (2006.01)
*C02F 1/32* (2023.01)

(52) U.S. Cl.
CPC .. *C02F 2201/3228* (2013.01); *C02F 2303/04* (2013.01)

(56) References Cited

U.S. PATENT DOCUMENTS

| | | | |
|---|---|---|---|
| 6,224,898 | B1 | 5/2001 | Balogh |
| 6,379,016 | B1 | 4/2002 | Boyd |
| 6,418,257 | B1 * | 7/2002 | Nath .................... G02B 6/032 385/125 |
| 6,440,405 | B1 | 8/2002 | Cooper |
| 6,447,537 | B1 | 9/2002 | Hartman |
| 6,579,906 | B2 | 6/2003 | Cooper |
| 7,569,181 | B2 | 8/2009 | Golden |
| 7,582,681 | B2 | 9/2009 | Schmaus |
| 8,512,723 | B2 | 8/2013 | Scholz |
| 8,545,084 | B2 | 10/2013 | Kim |
| 9,393,350 | B2 | 7/2016 | McGrath |
| 9,657,177 | B1 | 5/2017 | Pringle |
| 9,670,300 | B2 | 6/2017 | Olson |
| 9,829,604 | B2 * | 11/2017 | Schmidt ................ F24S 23/82 |
| 9,946,007 | B2 | 4/2018 | Sahlhoff |
| 10,125,251 | B2 | 11/2018 | Olson |
| 10,906,616 | B2 * | 2/2021 | Hietbrink ............ G02B 6/0055 |
| 2006/0051384 | A1 | 3/2006 | Scholz |
| 2006/0052452 | A1 | 3/2006 | Scholz |
| 2008/0075960 | A1 | 3/2008 | Pocius |
| 2008/0232135 | A1 | 9/2008 | Kinder |
| 2011/0309032 | A1 | 12/2011 | Maki |
| 2013/0048877 | A1 * | 2/2013 | Thoren ................. B08B 17/02 250/492.1 |
| 2013/0211310 | A1 | 8/2013 | Bommarito |
| 2014/0092632 | A1 | 4/2014 | Greener |
| 2014/0111851 | A1 | 4/2014 | Lin |
| 2015/0177432 | A1 * | 6/2015 | Hebrink .................. G02B 5/26 359/359 |
| 2015/0177441 | A1 | 6/2015 | Sherman |
| 2017/0182194 | A1 | 6/2017 | Shin |
| 2017/0281812 | A1 * | 10/2017 | Dobrinsky ............ B08B 9/0321 |
| 2018/0171157 | A1 | 6/2018 | Magin |
| 2018/0236113 | A1 * | 8/2018 | Gross ........................ A61L 2/26 |
| 2019/0310413 | A1 * | 10/2019 | Hietbrink ................ B08B 17/02 |
| 2021/0122667 | A1 * | 4/2021 | Westerhoff ............. G02B 6/001 |
| 2022/0026633 | A1 * | 1/2022 | Hebrink ................... A61L 2/10 |

FOREIGN PATENT DOCUMENTS

| | | |
|---|---|---|
| WO | WO2002-102244 | 12/2002 |
| WO | WO2007-087281 | 8/2007 |
| WO | WO2018-048654 | 3/2018 |

OTHER PUBLICATIONS

Davis, "Model of magnetorheological elastomers", Journal of Applied Physics, Mar. 1999, vol. 85, No. 6, pp. 3348-3351.
International Search Report for PCT International Application No. PCT/IB2019/061296, dated Apr. 20, 2020, 4 pages.

* cited by examiner

ULTRAVIOLET C LIGHT GUIDES

CROSS REFERENCE TO RELATED APPLICATIONS

This application is a national stage filing under 35 U.S.C. 371 of PCT/IB2019/061296, filed Dec. 23, 2019, which claims the benefit of U.S. Application No. 62/785,031, filed Dec. 26, 2018, the disclosure of which is incorporated by reference in its/their entirety herein.

BACKGROUND

Ultra-violet (UV) light is useful, for example, for disinfecting surfaces, articles, and fluids (e.g.; water and air). Ultra-violet light and high intensity blue light, however, tends to degrade most surfaces in varying degrees. In addition, ultra-violet C (UV-C) (i.e., 190 nm to 280 nm) light does not transmit through most materials. There is a need for surfaces that can transmit and withstand exposure to UV-C and blue light. The use of UV-C light for disinfecting hospital rooms and bathrooms is becoming more common. Most non-metal surfaces in the hospital room or bathroom, however, tend to degrade with prolonged exposure to UV-C light. Additional applications benefiting from disinfection with UV-C light guides include liquid drinking fountains, liquid drinking dispensers, water purification, and bio-pharmaceutical purification. Boat and ship hulls could also benefit from a UV-C light guides to prevent bio-fouling. There is a need for light guide materials which are transparent to UV-C and articles which can disinfect surfaces with UV-C light while not degrading those surfaces. Light guides are useful for conveying light from a light source to a surface or target. Light guides can be solid (e.g., quartz glass or fluoropolymer) or hollow (air).

SUMMARY

In one aspect, the present disclosure describes a light guide comprising a polymeric layer at least 25 (in some embodiments, at least 50, 60, 70, 80, 90, or even at least 95) percent transmissive over at least 30 nm bandwidth in a wavelength range from 180 to 280 (in some embodiments, 200 to 230 or 250 to 280) nm over a distance of at least 100 micrometers and visible light transparent UV-C reflecting layers (UV-C mirror) that are at least 50 percent (in some embodiments, at least 60, 70, 75, 80, 90, 95, or even at least 99) percent reflective over at least 30 nm bandwidth in a wavelength range from 180 to 280 (in some embodiments, 200 to 230 or 250 to 280) nm over an incident light angle of 0 to 90 degrees and that are at least 25 percent transmissive of visible light over at least 30 nm in wavelength range of 400 to 800 nm over an incident light angle of 0 to 90 degrees. The respective transmissive and reflective values are measured as described in the Examples.

Light guide described herein are useful, for example, for antimicrobial surfaces. Bacterial growth on surfaces and contact with surfaces is a primary means for spreading bacteria. In addition, bacteria create films, or colonies, on surfaces making them more difficult to remove. Irradiating bacteria with UV-C from beneath the surface rather than from above the surface will kill the cells attached to the surface making it an antimicrobial surface. UV-C light guides may be formed in the shape of a fiber, flexible rod, or rope for disinfecting the insides of surfaces (e.g., endoscopes, air ducts, and water ducts). Micro-structuring the surface of the light guide, for example, can provide a path for UV-C light to exit the light guide and disinfect the surface. Nano-structuring the micro-structured surface may also aid, for example, in UV-C light extraction and further reduce microbe adhesion to the surface. Anti-microbial additives to the UV-C light guide will enhance disinfection of the surface.

Light guide described herein are useful, for example, in water purification devices. Water drinking fountains and water dispensers are touched by hands of many different people and thus could benefit from disinfection of the surface between uses. Water purification processes frequently utilize 254 nm mercury bulbs for disinfecting water. Water purification designs can be improved, for example, with the UV-C light delivered to the water purification device with the light guide. Irradiation of the surface in contact with water with a low surface energy light guide will reduce, or even eliminate, bio-fouling of the surface in contact with the water. Transparent UV-C light guides having a transparent UV-C mirror on at least one surface enable viewing a water filter in the water purification device to visually determine if it is becoming fouled.

Light guides described herein are useful, for example, in endoscopes, air purification, and water purification.

DETAILED DESCRIPTION

Figure 1:
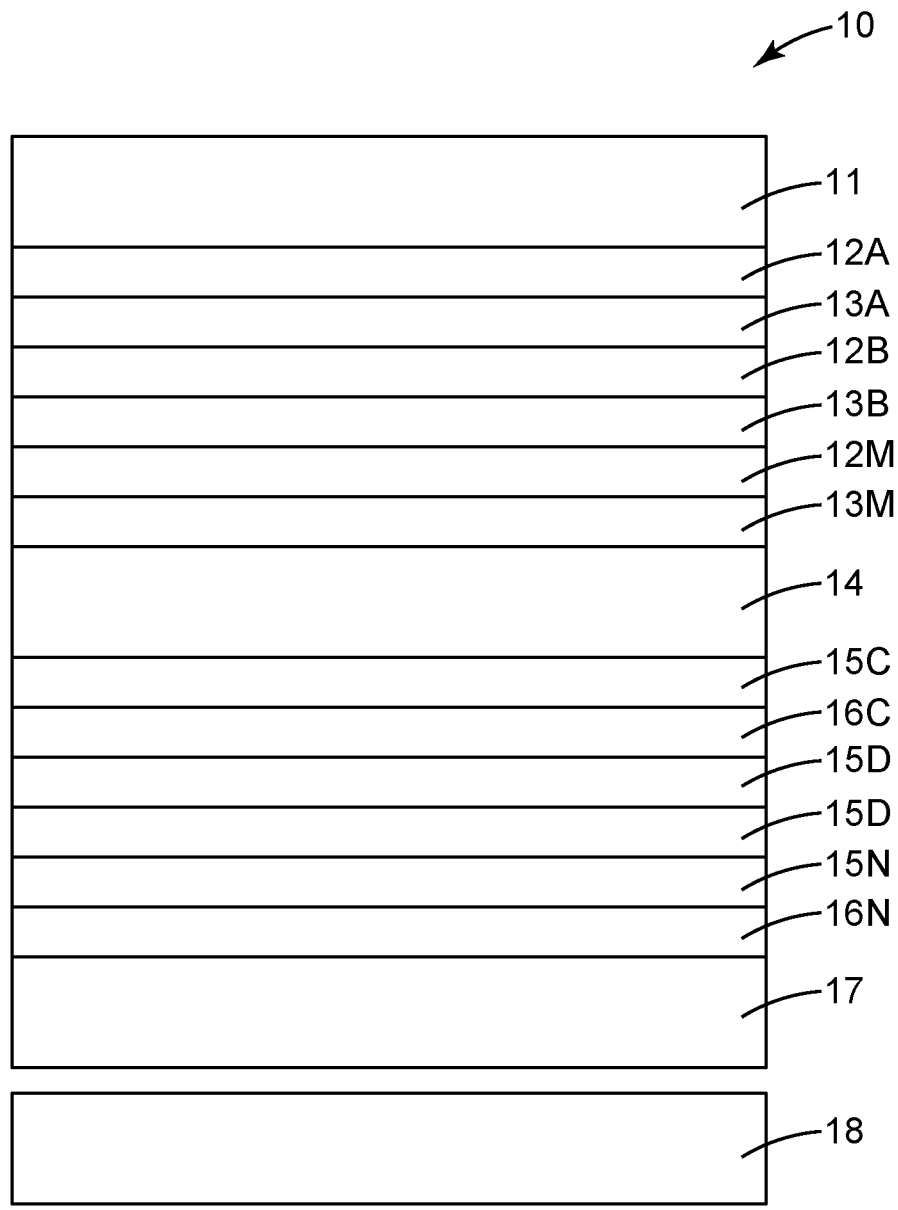
FIG. 1 is an exemplary solid UV-C light guide described herein comprising at least one transparent UV-C mirror.

In some embodiments, the polymeric layer comprises at least one of fluoropolymers, polyolefin copolymer, cyclic olefin copolymers, or cyclic olefin block copolymers. Exemplary fluoropolymers are available, for example under the trade designation "DYNEON THV220," "DYNEON THV230," "DYNEON THV2030," "DYNEON THV500," "DYNEON THV 610," and "DYNEON THV 815," from Dyneon LLC, Oakdale, MN Exemplary polyolefin copolymers are available, for example, under the trade designation "VIVION" from USI Group, Kaohsiung City, Taiwan. Exemplary polyolefin copolymers are available, for example, under the trade designation "TPX" from Mitsui Chemicals Americas, Rye Brook, NY Exemplary cyclic olefin copolymers are available, for example, under the trade designation "ZEONOR" from ZEON Corporation, Japan. Exemplary cyclic olefin block copolymers are available, for example, under the trade designation "TOPAS" from Polyplastics USA Inc., Farmington Hills, MI In some embodiments, the polymeric layer comprises fluoropolymer copolymers (e.g., fluoroethylenepolypropylene copolymer (FEP), perfluoroalkoxy (PFA), copolymer of tetrafluoroethylene, hexafluoropropylene, and vinylidene fluoride). Exemplary fluoropolymer copolymers are available, for example, under the trade designation "DYNEON FEP6322Z," "DYNEON FEP6307Z," "DYNEON FEP6305Z," and "DYNEON FEP6300GZ" from Dyneon LLC, Oakdale, MN The polymeric layer can be made using techniques generally known in the art, including extrusion, coextrusion, or coating. The polymeric light guide layer may also be surface structured by extrusion replication or embossing. The surface structure of the surface structured article described herein can be prepared by several methods. For example, a polymeric material may be extruded through a die capable of forming the patterned surface. In another example, the patterned surface may be formed by embossing techniques utilizing heat and/or pressure.

In some embodiments, making a surface structured article described herein utilizing an embossing technique comprises extruding or casting a polymeric film and contacting the polymeric film while it is still hot with an engraved, chilled cylinder that bears the negative structure of the desired patterned surface. The polymeric film may then be cooled, for example, on the cylinder. The substrate surface on which the coating composition is coated may have a structured surface provided when the substrate is made or may be subsequently added to the substrate surface (e.g., provided by techniques known in the art including extrusion replication, embossing, and casting, followed by, if needed, curing).

In some embodiments, the structured surface is a microstructured surface formed by an extrusion replication procedure utilizing a tool that imparts a negative structure in the polymer surface. The tooling can be in any of a variety of forms and materials. Typically, the tooling is a sheet, roll, belt, or roll of surface structured film made of metal or polymer. For metal tools, the metal is generally diamond-machined, embossed, knurled, or sandblasted to form the surface structure. The structured polymer surface can be formed, for example, by extrusion replication where a thermoplastic resin such as a fluoropolymer extruded through a die and into a nip with a machined metal tool roll and a rubber roll. The molten polymer can be quenched, for example, while in contact with the tool surface which then releases from the tool roll and is wound on a roll.

In some embodiments, the polymeric layer has a thickness of at least 5, 10, 50, 100, 500, 1000, 1500, 2000, 2500, or even at least 5000 (in some embodiments, in a range from 5 to 5000, 50 to 5000, 100 to 5000, 10 to 2500, 25 to 2500, 100 to 2500, or even 100 to 2000) micrometers.

The polymeric layer transmits at least 25 (in some embodiments, at least 50, 60, 70, 80, 90, or even at least 95) percent over at least 30 nm bandwidth in a wavelength range from 180 to 280 (in some embodiments, in a range from 200 to 230 or 250 to 280) nm over an incident angle of 0 to 90 degrees measured as described in the Examples.

In some embodiments, the reflecting layer is a dielectric mirror comprising alternating high refractive index inorganic and low refractive index inorganic layers, wherein the high refractive index inorganic layers have a refractive index greater than 1.6, and wherein the low refractive index inorganic layers have a refractive index less than 1.57. Higher reflectivity is achieved with greater refractive index differences between high refractive index inorganic layers and the low refractive index inorganic layers. Alternatively, more layers can be utilized to achieve higher reflective with smaller refractive index differences between high refractive index inorganic layers and the low refractive index inorganic layers. However, more layers can cause more light absorption which is undesirable, so greater refractive index difference between layers is preferred.

In some embodiments, the reflecting layer is a dielectric mirror comprising alternating inorganic and organic layers, wherein the inorganic layers have a refractive index greater than 1.6, and wherein the organic layers have a refractive index less than 1.57. Higher reflectivity is achieved with greater refractive index differences between high refractive index inorganic layers and the low refractive index inorganic layers. Alternatively, for example, more layers can be utilized to achieve higher reflective with smaller refractive index differences between high refractive index inorganic layers and the low refractive index inorganic layers. However, more layers can cause more light absorption which is undesirable, so greater refractive index difference between layers is preferred.

In some embodiments of multilayer optical films described herein, the first optical layer comprises polymeric material (e.g., at least one of polyvinylidene fluoride (PVDF), ethylene tetrafluoroethylene (ETFE)), and wherein the second optical layer comprises polymeric material (e.g., at least one of a copolymer (THV,) or a polyethylene copolymer comprising subunits derived from tetrafluoroethylene (TFE), hexafluoropropylene (HFP), and vinylidene fluoride (VDF), a copolymer (FEP) comprising subunits derived from tetrafluoro-ethylene (TFE) and hexafluoropropylene (HFP), or perfluoroalkoxy alkane (PFA)).

In some embodiments, the first optical layer is a fluoropolymer and the second optical layer is a fluoropolymer. Examples of the materials that are desirable for such embodiments include ETFE/THV, PMMA/THV, PVDF/FEP, ETFE/FEP, PVDF/PFA, and ETFE/PFA. In one exemplary embodiment, THV available, for example, under the trade designation "DYNEON THV 220 GRADE" or "DYNEON THV 2030 GRADE" or "DYNEON THV 815 GRADE" available from Dyneon LLC, Oakdale, MN, are employed as the second optical layer with PMMA as the first optical layer for multilayer UV mirrors reflecting 320-400 nm. In another exemplary embodiment, THV available, for example, under the trade designation "DYNEON THV 220 GRADE" or "DYNEON THV 2030 GRADE" or "DYNEON THV 815 GRADE" available from Dyneon LLC, Oakdale, MN, are employed as the second optical layer with "ELVALOY 1125" available from Dow, Midland, MI, as the first optical layer.

In some embodiments of multilayer optical films described herein, the first optical layer comprises inorganic material (e.g., at least one of titania, zirconia, zirconium oxynitride, hafnia, or alumina), and wherein the second optical layer comprises inorganic material (e.g., at least one of silica, aluminum fluoride, or magnesium fluoride). Exemplary materials are available, for example, from Materion Corporation, Mayfield Heights, OH, and Umicore Corporation, Brussels, Belgium. Dielectric mirrors, with optical thin film stack designs comprised of alternating thin layers of inorganic dielectric materials with refractive index contrast, can be used with multilayer optical films described herein. Depending upon the spectral region of interest, there are specific materials suitable for the region of UV-C reflection. Typically, these coatings are provided via one of two methods of physical vapor deposition (PVD) are used: evaporation or sputtering. Evaporated coatings rely upon heating the coating material (evaporant) to a temperature at which it evaporates. This is followed by condensation of the vapor upon a substrate. For evaporated dielectric mirror coatings, the electron-beam deposition process is most commonly used. Sputtered coatings use energetic gas ions to bombard a material ("target") surface, ejecting atoms which then condense on the nearby substrate. Depending upon which coating method is used, and the settings used for that method, thin film coating rate and structure-property relationships will be strongly influenced. Ideally, coating rates should be high enough to allow acceptable process throughput and film performance, characterized as dense, low stress, void free, non-optically absorbing coated layers.

Exemplary embodiments of UV-C mirrors can be designed to have peak reflectance at 254 nm, by both PVD methods. For example, coating discrete substrates by electron-beam deposition method, using $HfO_2$ as the high refractive index material and $SiO_2$ as the low refractive index material. Mirror design has alternating layers of "quarter wave optical thickness" (qwot) of each material, that are coated, layer by layer until, for example, after 13 layers the reflectance at 254 nm is >99%. The bandwidth of this reflection peak is around 80 nm. Quarter wave optical thickness is the design wavelength, here 254 nm, divided by 4, or 63.5 nm. Physical thickness of the high refractive index layers ($HfO_2$) is the quotient of qwot and refractive index of $HfO_2$ at 254 nm (2.41), or 30.00 nm. Physical thickness of the low refractive index layers ($MgF_2$), with 254 nm refractive index at 1.41, is 45.02 nm. Coating a thin film stack, then, which is comprised of alternating layers of $HfO_2$ and $SiO_2$ and designed to have peak reflectance at 254 nm begins by coating layer 1 $HfO_2$ at 30.00 nm. In electron beam deposition a four-hearth evaporation source is used. Each hearth is cone-shaped and 17 $cm^3$ volume of $HfO_2$ chunks fill it. The magnetically deflected high voltage electron beam is raster scanned over the material surface as filament current of the beam is steadily, in a pre-programmed fashion, increased. Upon completion of the pre-programmed step the $HFO_2$ surface is heated to evaporation temperature, about 2500° C., and a source shutter opens, the $HfO_2$ vapor flux emerging from the source in a cosine-shaped distribution and condensing upon the substrate material above the source. For enhancement of coating uniformity, the substrate holders rotate during deposition. Upon reaching the prescribed coating thickness (30.00 nm) the filament current shuts off; the shutter closes and the $HfO_2$ material cools. For layer 2 the evaporation source is then rotated to a hearth containing chunks of $MgF_2$ and a similar pre-programmed heating process begins. Here, the $MgF_2$ surface temperature is about 950° C. when the source shutter opens and, upon reaching the prescribed coating thickness (45.02 nm), the filament current shuts off; the shutter closes and the $HfO_2$ material cools. This step-wise process is continued, layer by layer, until the total number of design layers is reached. With this optical design, as total layers are increased, from 3 to 5 to 7 to 9 to 11 to 13 or more, the resulting peak reflectance increases accordingly, from 40% at 3 layers to >99% at 13 layers.

In another exemplary embodiment of UV-C reflective, visibly transparent film, UV transparent films can be coated in continuous roll to roll (R2R) fashion, using ZrON as the high refractive index material and $SiO_2$ as the low refractive index material. The optical design is the same type of thin film stack, alternating qwot layers of the two materials. For ZrON, with refractive index at 254 nm of 2.25, the physical thickness target was 28.22 nm. For $SiO_2$, here sputtered from an aluminum-doped silicon sputter target, with refractive index 1.49, the target thickness was 42.62 nm. Layer one ZrON is DC sputtered from a pure zirconium sputter target in a gas mixture of argon, oxygen and nitrogen. Whereas argon is the primary sputtering gas, oxygen and nitrogen levels are set to achieve transparency, low absorptance and high refractive index. The film roll transport initially starts at a pre-determined speed, and the sputter source power is ramped to full operating power, followed by introduction of the reactive gases and then achieving steady state condition. Depending upon the length of film to coat, the process continues until total footage is achieved. Here, as the sputter source is orthogonal to and wider than the film which is being coated, the uniformity of coating thickness is quite high. Upon reaching the desired length of coated film the reactive gases are set to zero and the target is sputtered to a pure Zr surface state. The film direction is next reversed and silicon (aluminum doped) rotary pair of sputter targets has AC frequency (40 kHz) power applied in an argon sputtering atmosphere. Upon reaching steady state, oxygen reactive gas is introduced to provide transparency and low refractive index. At the pre-determined process setting and line speed the second layer is coated over the length which was coated for layer one. Again, as these sputter sources are also orthogonal to and wider than the film being coated, the uniformity of coating thickness is quite high. After reaching the desired length of coated film the reactive oxygen is removed and the target is sputtered in argon to a pure silicon (aluminum doped) surface state. Layers three to five or seven or nine or eleven or thirteen, depending upon peak reflectance target, are coated in this sequence. Upon completion, the film roll is removed for post-processing.

These inorganic coatings can be provided, for example, by electron beam processes using a roll-to-roll (R2R), layer by layer coating sequence. For R2R sputtering of film, it is advantageous to use a sputtering system with multiple sources located around one, or perhaps two, coating drums. For example, for a thirteen layers optical stack design, a two, or even single, machine pass process, with alternating high and low refractive index layers coated sequentially, would be feasible. The number of machine passes needed is dependent, for example, on the machine design, cost, and practicality of thirteen consecutive sources. Additionally, coating rates would need to be matched to a single film line speed.

In some embodiments, the reflecting layer is a dielectric mirror comprising polyolefin copolymer layers having a refractive index greater than 1.46, and fluoropolymer layers having a refractive index less than 1.42. Higher reflectivity is achieved with greater refractive index differences between high refractive index inorganic layers and the low refractive index inorganic layers. Alternatively, for example, more layers can be utilized to achieve higher reflective with smaller refractive index differences between high refractive index inorganic layers and the low refractive index inorganic layers. However, more layers can cause more light absorption which is undesirable, so greater refractive index difference between layers is preferred.

Additional suitable polymers for the optical layers include polyolefin copolymers such as poly (ethylene-co-octene) (PE-PO) available, for example, under the trade designation "ENGAGE 8200" from Dow Elastomers, Midland, MI, polyethylene methyl acrylate also available, for example, under the trade designation "ELVALOY 1125" from Dow, Midland, MI, poly (propylene-co-ethylene) (PPPE) available, for example, under the trade designation "Z9470" from Atofina Petrochemicals, Inc., Houston, TX; and a copolymer of atactic polypropylene (aPP) and isotatctic polypropylene (iPP). The multilayer optical films can also include in the second layers, a functionalized polyolefin (e.g., linear lowdensity polyethylene-graft-maleic anhydride (LLDPE-g-MA) such as that available, for example, under the trade designation "BYNEL 4105" from E.I. duPont de Nemours & Co., Inc., Wilmington, DE).

In some embodiments, the reflecting layer is diffuse particle mirror. For example, calcium carbonate or barium sulfate particles can be blended into a fluoropolymer or polyolefin polymer film creating a refractive index difference between the incorporated particle and the host polymer film. Higher reflectivity is achieved with greater refractive index differences between high refractive index inorganic particle and the low refractive index polymeric host layer. Preferably, neither the polymer or the incorporated particle absorbs UV-C light. Nano-particles are preferred over micrometer sized particles for higher visible light transparency.

In some embodiments, the reflecting layers have a thickness of at least 20, 30 or even at least 40 (in some embodiments, in a range from 10 to 70, 20 to 60, or even 30 to 60) nanometers.

The reflecting layers reflect at least 50 percent (in some embodiments, at least 60, 70, 75, 80, 90, 95, or even at least 99) percent over at least 30 nm in a wavelength range from 180 to 280 (in some embodiments, in a range from 200 to 230 or 250 to 280) nm over an incident light angle of 0 to 90 degrees measured described in the Examples.

In some embodiments, the UV-C light guide comprises two sets of UV-C reflecting layers. The first set of UV-C reflecting layers has a first surface adjacent to a first surface polymer layer and a second surface adjacent to the solid polymer light guide. The second set of UV-C reflecting layers has a first surface adjacent to the first surface of a second surface polymer layer and a second surface adjacent to the solid polymer light guide. In order from top to bottom, the UV-C light guide comprises a first surface polymer layer, a first set of UV-C reflecting layers, a solid polymer light guide, a second set of UV-C reflecting layers, and a second surface polymer layer. The second surface polymer layer may optionally be an adhesive. In some embodiments, the first surface polymer layer, the solid polymer light guide, and the second surface polymer layer are fluoropolymers, or copolymers thereof. An optional adhesive layer can be adjacent to the second surface of the second surface polymer layer.

In some embodiments, light guides described herein further comprises a gas (e.g., air) gap disposed between the polymeric light guide layer and the reflecting layer. The gas layer can be provided with spacer posts which separate the polymeric light guide layer and the reflecting layer. The gas layer provides low UV-C light absorption and enables total internal reflection which increases the distance that UV-C light can travel through the UV-C light guide. Total internal reflection is reflection of the total amount of light at the interface of two media such as polymer and air. The posts can be micro-replicated by extrusion replication, or embossing, of the polymeric light guide layer. In some embodiments, the gas disposed between the polymeric layer and the reflecting layer has a thickness of at least 10, 100, or even 500; in some embodiments, in a range from 1 to 10, 100 to 1000, or even 200 to 500) nanometers.

In some embodiments, the UV-C light guide comprises at least two sets of UV-C reflecting layers. The first set of UV-C reflecting layers has a first surface adjacent to a first surface polymer layer and a second surface adjacent to a fluid (e.g., a liquid (e.g., an index matching fluid) or gas (e.g., air)) gap. The second set of UV-C reflecting layers has a first surface adjacent to the first surface of a second surface polymer layer and a second surface adjacent to the fluid gap. In order from top to bottom, the UV-C light guide comprises a first surface polymer layer, a first set of UV-C reflecting layers, a fluid (e.g., a liquid (e.g., an index matching fluid) or gas (e.g., air)) gap, a second set of UV-C reflecting layers, and a second surface polymer layer. The second surface polymer layer may optionally be an adhesive. In some embodiments, the first surface polymer layer and the second surface polymer layer are fluoropolymers, or copolymers thereof. An optional adhesive layer can be adjacent to the second surface of the second surface polymer layer and adjacent to the first surface of the first polymer layer. In some embodiments, the first set of UV-C reflecting layers has less reflectivity (e.g., <80%) than the reflectivity (e.g., >80%) of the second set of UV-C reflective layers.

In some embodiments, the UV-C light guide comprises two sets of UV-C reflecting layers. The first set of UV-C reflecting layers has a first surface adjacent to a first surface polymer layer and a second surface adjacent to a second polymer layer. The second set of UV-C reflecting layers has a first surface adjacent to the first surface of a third surface polymer layer and a second surface adjacent to a fourth polymer layer. In order from top to bottom, the UV-C light guide comprises a first surface polymer layer, a first set of UV-C reflecting layers, a second polymer layer, a fluid (e.g., a liquid (e.g., an index matching fluid) or gas) fluid (e.g., a liquid (e.g., an index matching fluid) or gas (e.g., air)) gap, a third polymer layer, a second set of UV-C reflecting layers, and a second surface adjacent to a fourth polymer layer. In some embodiments, the first surface polymer layer, the second polymer layer, the third polymer, and the fourth polymer layer are fluoropolymers, or copolymers thereof. An optional adhesive layer can be adjacent to the first surface of the first polymer layer and the second surface of the fourth polymer layer. In some embodiments, the first set of UV-C reflecting layers has less reflectivity (e.g., <80%) than the reflectivity (e.g., >80%) of the second set of UV-C reflective layers.

In some embodiments, light guides described herein further comprise porous material (e.g., nanosilica, microvoided polymer, and nano-voided polymer) gap disposed between the polymeric layer and the reflecting layer. Exemplary porous materials are available, for example, under the trade designation "IPN-NANO" from Kingspan, Arlington, VA and under the trade designation "NANOPORE" from Nanopore Inc., Albuquerque, NM Exemplary porous materials are available, for example, under the trade designation "LIQUI-FLUX" from 3M Deutschland GmbH, Wuppertal, Germany. Porous materials have a lower refractive index than solid materials. Lower refractive index tends to maintain total internal reflection of light in the solid material for incident light at an angle greater than the critical angle required for total internal reflection.

In some embodiments, the polymeric layer has first and second opposed major surfaces, and wherein at least one of the first or second major surface of the polymeric layer has a structured surface. Light extraction surface structures which decrease the incident light angle from that which is critical for total internal reflection (TIR) are desired on the anti-microbial surface. The critical angle can be calculated from Snell's law. Using Snell's law for a polymer having a refractive index of 1.35 and air having a refractive index of 1.0, the critical angle can be calculated to be 47.8 degrees. Incident light angles of less than 47.8 degrees from normal to the surface refract a portion of the light through the surface. Incident light angles greater than 47.8 degrees from normal to the surface reflect back into the polymer light guide. For non-normal light incidence, reflection and transmission coefficients can be calculated from Fresnel equations. The light extraction surface structures can be random (matte finish) or engineered surfaces structures. Both random and engineered surface structures can be created with thermal embossing or extrusion replication. Light extraction surface structures are described, for example, in U.S. Pat. No. 8,545,084 (Kim et. al.) and U.S. Pat. No. 9,946,007 (Sahlhoff et. al.). In some embodiments, it is desired to have a gradient to the spacing, or shape, of the surface structure to increase the distance light will travel through the light guide. It can also be beneficial for the light guide to have a taper, or wedge shape, as described, for example, in U.S. Pat. No. 6,379,016 (Boyd et. al.). In some embodiments, light guides described herein have a thickness of at least 10, 25, 50, 100, 500, 1000, 1500, 2000, 2500, or even at least 5000 (in some embodiments, in a range from 10 to 5000, 25 to 5000, 100 to 5000, 10 to 2500, 25 to 2500, 100 to 2500, or even 100 to 2000) micrometers.

In some embodiments external layers have engineered structures that reduce or prevent bacterial adhesion. Exemplary engineered structures are disclosed in U.S. Pat. Pub. Nos. US2013/0211310 (Bommarito et. al.) and US2018/00171157 (Magin et. al.).

In some embodiments, light guides described herein have first and second opposed sides further comprises UV-C light sources (e.g., LED) embedded on at least side edge of the light guide, wherein the UV-C light sources are position such that when energized provide UCV light within the light guide. In a lightguide, the maximum acceptance angle for incident rays is defined as numerical aperture. Light or radiant energy within this critical angle is propagated along the waveguide. Light entering the light guide at an angle greater than the maximum angle will exit the side of the guide. The numerical aperture value is dimensionless. It is calculated by taking the sin of the maximum acceptance angle $$NA = \frac{1}{n_0}\sqrt{n_{core}^2 - n_{cladding}^2}$$

where NA is numerical aperture, no is refractive index of fluid (e.g., air or water), $n_{core}$ is refractive index of light guide, and $n_{cladding}$ is refractive index of surface layer interfacing fluid.

In some embodiments, light guides described herein further comprises an array of UV-C light sources (e.g., LED) embedded in the polymer layer facing away from the reflecting layers. Light emitting diodes (LEDs) can be spaced, for example, equidistant in an array at the bottom plane of the UV-C light guide. Desired spacing of the LEDs is impacted by their UV-C energy output and the desired UV-C energy (intensity) at the surface of the UV-C light guide for anti-microbial effectiveness.

In some embodiments, light guides described herein further comprises adhesive, wherein the polymeric layer and the reflecting layer each have first and second opposed major surfaces, wherein the second major surface of the polymeric layer is adjacent to the first major surface of the reflecting layer, and wherein the adhesive is disposed on the second major surface of the reflecting layer. Exemplary adhesives are known in the art and include acrylic pressure sensitive adhesives (PSAs) and silicone PSAs. An exemplary PSA is an optically clear adhesive (available under the trade designation "OCA8171" from 3M Company, St. Paul, MN).

Extrudable pressure sensitive adhesives are available, for example, from Kuraray, Osaka, Japan, under the trade designations "LIR-290," LA2330," "LA2250," "LA2140E," and "LA1114;" and Exxon Mobil, Irving, TX, under the trade designation "ESCORE."

Exemplary extrudable adhesives for the optional fourth layer include isobutylene/isoprene copolymers which are available, for example, from Exxon Mobil Corp., under the trade designations "EXXON BUTYL 065," "EXXON BUTYL 068," and "EXXON BUTYL 268" (believed to have unsaturation in the range of about 1.05 to about 2.30 mole percent); United Chemical Products, Velizy-Villacoublay, France, under the trade designation "BK-1675N" (believed to have an unsaturation of about 1.7 mole percent); LANXESS, Sarnia, Ontario, Canada, under the trade designation "LANXESS BUTYL 301" (believed to have an unsaturation of about 1.85 mole percent), "LANXESS BUTYL 101-3" (believed to have an unsaturation of about 1.75 mole percent), and "LANXESS BUTYL 402" (believed to have an unsaturation of about 2.25 mole percent); and Kaneka, Osaka, Japan, under the trade designation "SIBSTAR" (available as both diblocks and triblocks with the styrene content believed to varying from about 15 to about 30 mole percent, based on the mole of the copolymer).

Exemplary polyisobutylene resins are available, for example, from Exxon Chemical Co., Irving, TX, under the trade designation "VISTANEX;" Goodrich Corp., Charlotte, NC, under the trade designation "HYCAR;" and Japan Butyl Co., Ltd., Kanto, Japan, under the trade designation "JSR BUTYL."

In general, suitable polyisobutylenes may have a wide variety of molecular weights and a wide variety of viscosities. In some embodiments, the polyisobutylene has a weight average molecular weight (as measured by Gel Permeation Chromatography using polystyrene standards) of at least about 300,000 (in some embodiments, at least 400,000, or even at least 500,000) grams per mole. In some embodiments, the polyisobutylene has a weight average molecular weight of less than 300,000 (in some embodiments, up to 280,000, 275,000, 270,000, 260,000, 250,000, 240,000, 230,000, 220,000, 210,000, or up to 200,000) grams per mole. In some embodiments, when defined by the viscosity as measured by intrinsic viscosity at 20° C. in diisobutylene, the polyisobutylene has a viscosity average molecular weight in a range from 100,000 to 10,000,000 (in some embodiments, in a range from 500,000 to 5,000,000) grams per mole. Polyisobutylenes of many different molecular weights and viscosities are available. In some embodiments, the molecular weight of the polyisobutylene changes during the process of making a PSA.

In some embodiments, for PSAs comprising polyisobutylene, the PSA further comprises a hydrogenated hydrocarbon tackifier (in some embodiments, a poly(cyclic olefin)). In some embodiments, the hydrogenated hydrocarbon tackifier is present in a range from 5 to 90 percent by weight, based on the total weight of the PSA composition. In some embodiments, poly(cyclic olefin) is blended with 10 to 95 percent by weight polyisobutylene, based on the total weight of the PSA composition. In some embodiments, the PSA comprises hydrogenated hydrocarbon (e.g., poly(cyclic olefin)) tackifier in a range from 5 to 70 weight percent, based on the total weight of the PSA composition and 30 to 95 weight percent polyisobutylene, based on the total weight of the PSA composition. In some embodiments, a hydrogenated hydrocarbon tackifier (in some embodiments, the poly(cyclic olefin)) is present in an amount of less than 20 (in some embodiments, less than 15) percent by weight, based on the total weight of the PSA composition. For example, the hydrogenated hydrocarbon tackifier (in some embodiments, the poly(cyclic olefin)) may be present in a range from 5 to 19.95, 5 to 19, 5 to 17, 5 to 15, 5 to 13, or even 5 to 10 percent by weight, based on the total weight of the PSA composition. In some embodiments, the PSA is free of acrylic monomers and polyacrylates. Exemplary polyisobutylene PSAs include adhesive compositions comprising a hydrogenated poly(cyclic olefin) and a polyisobutylene resin such as those reported in PCT Pub. No. WO 2007/087281 (Fujita et al.), the disclosure of which is incorporated herein by reference.

Exemplary hydrogenated hydrocarbon tackifiers for the optional fourth layer are available, for example, from Arakawa Chemical Industries Co., Ltd., Osaka, Japan, under the trade designations "ARKON P" and "ARKON M." These materials are described in the trade literature as being water white, hydrogenated hydrocarbon resins. Hydrogenated hydrocarbon tackifiers under the trade designation "ARKON P" (e.g., P-70, P-90, P-100, P-115, and P-140) are said to be fully hydrogenated, while those under the trade designation "ARKON M" (e.g., M-90, M-100, M-115, and M-135) are partially hydrogenated. The hydrogenated hydrocarbon tackifier available under the trade designation "ARKON P-100" is said to have a number average molecular weight of about 850 grams/mole, a softening point of about 100° C., and a glass transition temperature of about 45° C. The hydrogenated hydrocarbon tackifier available under the trade designation "ARKON P-140" has a number average molecular weight of about 1250 grams/mole, a softening point of about 140° C., and a glass transition temperature of about 90° C. The hydrogenated hydrocarbon tackifier available under the trade designation "ARKON M-90" has a number average molecular weight of about 730 grams/mole, a softening point of about 90° C., and a glass transition temperature of about 36° C. The hydrogenated hydrocarbon tackifier available under the trade designation "ARKON-M-100" has a number average molecular weight of about 810 grams/mole, a softening point of about 100° C., and a glass transition temperature of about 45° C.

Other exemplary hydrogenated hydrocarbon tackifiers for the optional fourth layer are available, for example, from Exxon Chemical under the trade designations "ESCOREZ 1315," "ESCOREZ 1310LC," "ESCOREZ 1304," "ESCOREZ 5300," "ESCOREZ 5320," "ESCOREZ 5340," "ESCOREZ 5380," "ESCOREZ 5400," "ESCOREZ 5415," "ESCOREZ 5600," "ESCOREZ 5615," "ESCOREZ 5637," and "ESCOREZ 5690."

The "1300" series resins are described in the trade literature as being aliphatic resins with a high softening point. The "ESCOREZ 1315" resin is said to have a weight average molecular weight of about 2200 grams/mole, a softening point in the range of about 112° C. to about 118° C., and a glass transition temperature of about 60° C. The "ESCOREZ 1310LC" resin is said to have a light color, a weight average molecular weight of about 1350 grams/mole, a softening point of about 95° C., and a glass transition temperature of about 45° C. The "ESCOREZ 1304" resin is said to have a weight average molecular weight of about 1650 grams/mole, a softening point in the range of about 97° C. to about 103° C., and a glass transition temperature of about 50° C.

The "5300" series of resins are described in the trade literature as being water white, cycloaliphatic hydrocarbon resins, and have a weight average molecular weight in the range of about 370 grams/mole to about 460 grams/mole, a softening point in the range of about 85° C. to about 140° C., and a glass transition temperature in the range of about 35° C. to about 85° C.

The "5400" series of resins are described in the trade literature as being very light colored cycloaliphatic hydrocarbon resins and have a weight average molecular weight in the range of about 400 grams/mole to about 430 grams/mole, a softening point in the range of about 103° C. to about 118° C., and a glass transition temperature in the range of about 50° C. to about 65° C.

The "5600" series of resins are described in the trade literature as being very light colored, aromatic modified cycloaliphatic resins, where the percent of aromatic hydrogen atoms is in the range of about 6 to about 12 weight percent based on the weight of all the hydrogen atoms in the resins. Further, the "5600" series of resins are said to have a weight average molecular weight in the range of about 480 grams/mole to about 520 grams/mole, a softening point in the range of about 87° C. to about 133° C., and a glass transition temperature in the range of about 40° C. to about 78° C.

Other exemplary suitable hydrogenated hydrocarbon tackifiers for the optional fourth layer are available, for example, from Eastman, Kingsport, TN, under the trade designations "REGALREZ 1085," "REGALREZ 1094," "REGALREZ 1126," "REGALREZ 1139," "REGALREZ 3102," and "REGALREZ 6108." These resins are described in the trade literature as hydrogenated aromatic pure monomer hydrocarbon resins. They have a weight average molecular weight ranging from about 850 grams/mole to about 3100 grams/mole, a softening temperature in the range of about 87° C. to about 141° C., and a glass transition temperature in the range of about 34° C. to about 84° C. The "REGALEZ 1018" resin can be used in applications that do not generate heat. This tackifying resin has a weight average molecular weight of about 350 grams/mole, a softening point of about 19° C., and a glass transition temperature of about 22° C.

Other exemplary suitable hydrogenated hydrocarbon tackifiers for the optional fourth layer are available, for example, from Cray Valley, Exton, PA, under the trade designations "WINGTACK 95" and "WINGTACK RWT-7850." The trade literature describes these tackifying resins as synthetic resins obtained by cationic polymerization of aliphatic C5 monomers. The tackifying resin available under the trade designation "WINGTACK 95" is a light-yellow solid with a weight average molecular weight of about 1700 grams/mole, a softening point of 98° C., and a glass transition temperature of about 55° C. The tackifying resin available under the trade designation "WINGTACK RWT-7850" is a light-yellow solid with a weight average molecular weight of about 1700 grams/mole, a softening point of about 102° C., and a glass transition temperature of 52° C.

Other exemplary hydrogenated hydrocarbon tackifiers for the optional fourth layer are available, for example, from Eastman, under the trade designations "PICCOTAC 6095-E," "PICCOTAC 8090-E," "PICCOTAC 8095," "PICCOTAC 8595," "PICCOTAC 9095," and "PICCOTAC 9105." The trade literature describes these resins as aromatic modified, aliphatic hydrocarbon resin or as aromatic modified C5 resins. The tackifier available under the trade designation "PICCOTACK 6095-E" has a weight average molecular weight of about 1700 grams/mole and a softening point of about 98° C. The tackifier available under the trade designation "PICCOTACK 8090-E" has a weight average molecular weight of about 1900 grams/mole and a softening point of about 92° C. The tackifier available under the trade designation "PICCOTACK 8095" has a weight average molecular weight of about 2200 grams/mole and a softening point of about 95° C. The tackifier available under the trade designation "PICCOTAC 8595" has a weight average molecular weight of about 1700 grams/mole and a softening point of about 95° C. The tackifier available under the trade designation "PICCOTAC 9095" has a weight average molecular weight of about 1900 grams/mole and a softening point of about 94° C. The tackifier available under the trade designation "PICCOTAC 9105" has a weight average molecular weight of about 3200 grams/mole and a softening point of about 105° C.

In some embodiments, the hydrogenated hydrocarbon tackifier is a hydrogenated poly(cyclic olefin) polymer. Poly(cyclic olefin) polymers generally have low moisture permeability and can impact the adhesive properties of the polyisobutylene resin, for example, by functioning as a tackifier. Exemplary hydrogenated poly(cyclic olefin) polymers include hydrogenated petroleum resins; hydrogenated terpene-based resins (e.g., available from Yasuhara Chemical, Hiroshima, Japan, under the trade designation "CLEARON," in grades P, M, and K); hydrogenated resin or hydrogenated ester-based resins (available, for example, from Hercules Inc., Wilmington, DE, under the trade designations "FORAL AX" and "FORAL 105;" and from Arakawa Chemical Industries Co., Ltd., Osaka, Japan, under the trade designations "PENCEL A," "ESTERGUM H," and "SUPER ESTER A"); disproportionate resins or disproportionate ester-based resins (available, for example, from Arakawa Chemical Industries Co., Ltd., under the trade designation "PINECRYSTAL"); a hydrogenated dicyclopentadiene-based resin (e.g., a hydrogenated C5-type petroleum resin obtained by copolymerizing a C5 fraction such as pentene, isoprene, or piperine with 1,3-pentadiene produced through thermal decomposition of petroleum naphtha (available, for example, from Exxon Chemical Co., under the trade designations "ESCOREZ 5300" and "ESCOREZ 5400" and from Eastman Chemical Co., under the trade designation "EASTOTAC H")); a partially hydrogenated aromatic modified dicyclopentadiene-based resin (available, for example, from Exxon Chemical Co., under the trade designation "ESCOREZ 5600"); a resin resulting from hydrogenation of a C9-type petroleum resin obtained by copolymerizing a C9 fraction such as indene, vinyltoluene and α- or β-methylstyrene produced by thermal decomposition of petroleum naphtha (available, for example, from Arakawa Chemical Industries Co., Ltd., under the trade designations "ARCON P" or "ARCON M"); and a resin resulting from hydrogenation of a copolymerized petroleum resin of the above-described C5 fraction and C9 fraction available, for example, from Idemitsu Petrochemical Co., Tokyo, Japan, under the trade designation "IMARV." In some embodiments, the hydrogenated poly(cyclic olefin) is a hydrogenated poly(dicyclopentadiene), which may provide advantages to the PSA (e.g., low moisture permeability and transparency).

The hydrogenated hydrocarbon tackifier generally has a solubility parameter (SP value), which is an index for characterizing the polarity of a compound, that is similar to that of the polyisobutylene and exhibits good compatibility (i.e., miscibility) with the polyisobutylene so that a transparent film can be formed. The tackifying resins are typically amorphous and have a weight average molecular weight no greater than 5000 grams/mole. If the weight average molecular weight is greater than about 5000 grams/mole, compatibility with the polyisobutylene material may decrease, tackiness may decrease, or both. The molecular weight is often no greater than 4000 (in some embodiments, no greater than 2500, 2000, 1500, 1000, or even no greater than 500; in some embodiments, the molecular weight is in a range from 200 to 5000, 200 to 4000, 200 to 2000 or even 200 to 1000) gram/mole.

PSA layers can be provided by techniques known in the art, such as hot melt extrusion of an extrudable composition comprising the components of the PSA composition. Advantageously, the PSA layer can be made by this process in the absence of solvents. Exemplary methods for making extrudable adhesives are described, for example, in PCT Pub. No. WO1995/016754A1 (Leonard et al.), the disclosure of which is incorporated herein by reference.

In some embodiments, PSAs for the fourth layer comprise at least one of a UV absorber (UVA), a HALS, or an antioxidant. Exemplary UVAs include those described above in conjunction with multi-layer film substrates (e.g., those available from Ciba Specialty Chemicals Corporation, under the trade designations "TINUVIN 328," "TINUVIN 326," "TINUVIN 783," "TINUVIN 770," "TINUVIN 479," "TINUVIN 928," "TINUVN 1577," and "TINUVIN 1600"). In some embodiments, UVAs, when used, are present in a range from about 0.01 to about 10 percent by weight, based on the total weight of the PSA composition. Exemplary embodiments of UVAs for pressure sensitive adhesives include UVA oligomers as described in U.S. Pat. No. 9,670,300 (Olson et. al. et al.) and U.S. Pat. No. 10,125,251 (Olson et al.), the disclosures of which is incorporated herein by reference.

Exemplary antioxidants include hindered phenol-based compounds and phosphoric acid ester-based compounds, and those described above in conjunction with multi-layer film substrates (e.g., those available from Ciba Specialty Chemicals Corporation, under the trade designations "IRGANOX 1010," "IRGANOX 1076", and "IRGAFOS 126" and butylated hydroxytoluene (BHT)). In some embodiments, antioxidants, when used, are present in a range from about 0.01 to about 2 percent by weight, based on the total weight of the PSA composition.

Exemplary stabilizers include phenol-based stabilizers, hindered amine-based stabilizers (e.g., those described above in conjunction with multi-layer film substrates and those available from BASF under the trade designation "CHIMASSORB 2020"), imidazole-based stabilizers, dithiocarbamate-based stabilizers, phosphorus-based stabilizers, and sulfur ester-based stabilizers. In some embodiments, such compounds, when used, are present in a range from about 0.01 to about 3 percent by weight, based on the total weight of the PSA composition.

The components articles described herein can be assembled using techniques generally known in the art (see, in general, for example, adhesive lamination, heat lamination in a hot press, roll to roll thermal lamination with a hot can and nip roll, or injection molding).

In some embodiments, light guides described herein further comprises an adhesive primer to promote adhesion of the adhesive to the bottom side of the UV-C light guide. Exemplary adhesive primers include nano-silica and other nano-particles. Nano-structures created by refractive ion etching methods are also effective surface primers for adhesives. Corona treatment of the polymer light guide surface in the presence of air, nitrogen, or acetone can also provide increased adhesion of an adhesive to the polymer light guide.

In some embodiments, light guides described herein further comprises a removable liner on the adhesive layer. Exemplary adhesives are known in the art and discussed above.

In some embodiments, the polymeric layer and the reflecting layer each have first and second opposed major surfaces, wherein the second major surface of the polymeric layer is adjacent to the first major surface of the reflecting layer, and wherein the second major surface of the reflecting layer is attached to a substrate (e.g., a graphic film, or a polymer, paint, wood (including artificial or simulated), or stone (including artificial or simulated) surface including; ceiling, wall, floor, or counter top). A "graphic film," as used herein, is any film that absorbs at least some visible or infrared light range and reflects at least some wavelengths of light in the visible range where the reflected light contains some graphical content. The graphical content may include patterns, images, or other visual indicia. The graphic film may be a printed film, or the graphic film may be created by means other than printing. For example, the graphic film may be perforated reflective film with a patterned arrangement of perforations. The graphic film may also be created by embossing. In some embodiments, the graphic film is a partially transmissive graphic film. Exemplary graphic films are available under the trade designation "DINOC" by 3M Company.

In some embodiments, light guides described herein are in the shape of a tube. In some embodiments, light guides described herein are in the shape of a rod.

In some embodiments, light guides described herein can be wrapped around a 1 cm diameter rod without breaking.

In some embodiments, light guides described herein further comprises an antimicrobial additive. In some embodiments, antimicrobials preferably have little or no absorbance in the UV-C region of 200 nm to 300 nm, and may be selected from metals, metal oxides, cationic surfactants free of aromatic groups, cationic antimicrobial polymers, antimicrobial lipids, and alkyl carboxylic acids and alkyl carboxylate ester carboxylic acids. The antimicrobial also may be generated in-situ by exposure to the UV light. Silver is also known to be an effective antiseptic and has been used in creams to treat wounds and other topical infections. The active form of silver is the ion Ag+. Similarly, copper and zinc have antimicrobial activity and it is believed that the ions are the active components ($Cu^{2+}$, $Zn^{2+}$). These ions may be delivered from a variety of salts and complexes including silver zeolites; inorganic silver salts (e.g., silver nitrate, silver chloride, silver sulfate, silver thiosulfate; silver phosphate, silver alkyl, silver aryl, and silver aralkyl carboxylates (e.g., carboxylate anions have less than 8 carbon atoms (e.g., the acetate, lactate, salicylate, and gluconate salts)); silver oxide, colloidal silver, nanocrystalline silver, silver coated microspheres, silver complexed with various polymers, as well as silver delivered from dendrimers as reported, for example, in U.S. Pat. No. 6,579,906 (Cooper et al.) and U.S. Pat. No. 6,224,898 (Balogh et al.), the disclosures of which are incorporated herein by reference; and silver antimicrobial complexes (e.g., silver sufadiazine). The silver may optionally be complexed with primary, secondary, tertiary, and quaternary amines, as well as polymeric forms thereof, and silver protein complexes. Similarly, these same salts and complexes of copper or zinc may be used (e.g., copper chloride or zinc chloride). Those compounds of this class that may be, for example, vacuum deposited, may be coated on the external surface of the device, as described U.S. Pat. No. 9,393,350 (McGrath et al.), the disclosure of which is incorporated herein by reference. Antimicrobial polymers comprising quaternary amine or protonated primary, secondary, or tertiary amine groups may also be used as the antiseptic.

For UV stability, a desirable cationic antimicrobial polymer is a polyquaternary amine. Polyquaternary amines are typically polymers having quaternary amine groups with at least one alkyl or aralkyl chain of at least 6 carbon atoms (in some embodiments, at least 8 carbon atoms). The polymers may be linear, branched, hyperbranched or dendrimers. Exemplary antimicrobial polymeric quaternary amine polymers include those described in U.S. Pat. No. 6,440,405 (Cooper et al.), U.S. Pat. No. 5,408,022 (Imazato et al.), and U.S. Pat. No. 5,084,096 (Stovicek et al.); PCT Pub. No. WO/02102244, published Dec. 27, 2002; and *Disinfection, Sterilization and Preservation*, S. Block, 4th ed., 1991, Chapter 13, Lea & Febiger, the disclosures of which are incorporated herein by reference.

A useful class of polymeric protonated amine antiseptic compounds are polybiguanides. Compounds of this class are represented by the formula:

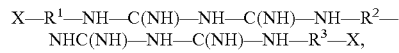

where $R^1$, $R^2$, and $R^3$ are bridging groups such as polymethylene groups (in some embodiments, having 2 to 10, 4 to 8, or even 6 methylene groups). The methylene groups can be optionally substituted in available positions with halogen, hydroxyl, or phenyl groups. X is a terminal group and is typically an amine, an amine salt, or a dicyandiamide group. In some embodiments, a compound of this class is polyhexamethylene biguanide (PHMB) (available, for example, under the trade designation "COSMOCIL CQ" from Aveci, Wilmington, DE).

Alternatively, for example, antimicrobial cationic surfactants can be used. This class of compounds typically comprise at least one quaternary ammonium groups, wherein attached to the quaternary ammonium group is at least one C6-C18 linear or branched alkyl chain. Suitable compounds include those disclosed in *Disinfection, Sterilization and Preservation*, S. Block, 4th ed., 1991, Chapter 13, Lea & Febiger. Particularly preferred compounds of this class have one or two C8-C18 alkyl or aralkyl chains and may be represented by the following formula:

where $R^1$ and $R^2$ are C1-C18 linear or branched alkyl, alkaryl chains that may be substituted in available positions by N, O, or S, provided at least one $R^1$ or $R^2$ is a C8-C18 linear or branched alkyl chain that may be substituted in available positions by N, O, or S. $R^3$ and $R^4$ are C1-C6 alkyl groups. $R^3$ and $R^4$ may also form a ring (e.g., a pyridine ring with the nitrogen of the quaternary ammonium group). X is an anion (e.g., a halide (e.g., Cl— or Br—)). Other anions may include methosulfate, ethosulfate, and phosphates. In some embodiments of this class include monoalkyltrimethylammonium salts, monoalkyldimethylbenzyl ammonium salts, dialkyldimethyl ammonium salts, benzethonium chloride, and octenidine.

Exemplary quaternary ammonium antiseptics include dimethyldialkylammonium halides where the alkyl groups have chain lengths of C8-C18, an example of which is available under the trade designation "BARQUAT 4250" from Lonza, Allendale, NJ A mixture of chain lengths (e.g., a mixture of dioctyl, dilauryl, and dioctadecyl) may also be useful. Exemplary compounds include quaternary ammonium salts (available, for example, under the trade designations "BARDAC 2050," "BARDAC 205M," and "BAR- DAC 2250" from Lonza); cetylpyridinium halides (e.g., cetylpyridinium chloride (available, for example, under the trade designation "CEPACOL CHLORIDE" from Merrell Labs, Kansas City, MO)); and octenidine.

In some embodiments, the outermost layer includes at least one antiseptic at a suitable level to produce the desired result. In some embodiments, compositions include a total amount of antiseptic of at least 0.2 (in some embodiments, at least 0.25, 0.3, 0.35, 0.4, 0.45, 0.5, 0.75, 1, 2, or even at least 3) wt. %, based on the total weight of the outermost layer. Alternatively, the antiseptic can be coated onto the outermost layer.

Additional antiseptics for use with those described herein include peroxides, C6-C14 alkyl carboxylic acids and alkyl ester carboxylic acids, antimicrobial natural oils, and compatible combinations thereof (see, e.g., U.S. Pat. Pub. No. US2006/0051384 A1 (Scholz et al.)), the disclosure of which is incorporated herein by reference; and diphenyl ethers, phenols, halogenated phenols, bisphenols, resorcinols and its derivatives, anilides, and combinations thereof (see, e.g., U.S. Pat. Pub. No. US2006/0052452 A1 (Scholz)), the disclosure of which is incorporated herein by reference.

Also contemplated are top or external coating or layers which control biofilm and bacterial adhesion. Exemplary coatings include those described in U.S. Pat. Pub. No. US2008/0075960 (Pocius et al.), the disclosure of which is incorporated herein by reference.

In some embodiments, the antiseptics include an effective amount of an antimicrobial lipid antiseptic comprising a (C7-C14) saturated fatty acid ester of a polyhydric alcohol, an (C8-C22) unsaturated fatty acid ester of a polyhydric alcohol, a (C7-C14) saturated fatty ether of a polyhydric alcohol, an (C8-C22) unsaturated fatty ether of a polyhydric alcohol, C8-C14 alkylcarboxylates, and C5-C12 1,2 alkane diol. Alkoxylated derivatives thereof, wherein the alkoxylated derivative has less than 5 moles of alkoxide per mole of polyhydric alcohol may also be used; with the proviso that for polyhydric alcohols other than sucrose, the esters comprise monoesters and the ethers comprise monoethers, and for sucrose the esters comprise monoesters, diesters, or combinations thereof, and the ethers comprise monoethers, diethers, or combinations thereof. Useful antiseptics of this class are further described, for example, in U.S. Pat. No. 8,512,723 (Scholz et al.) and U.S. Pat. No. 7,582,681 (Schmaus et al.), the disclosures of which are incorporated herein by reference.

An exemplary class of antimicrobial antiseptics comprise C6-C14 alkyl carboxylic acids and alkyl carboxylate ester carboxylic acids, which include C6-C14 (in some embodiments, C8-C12) straight chain or branched alkyl carboxylic acids (e.g., heptanoic, carpic, caprylic, undecylenic, and lauric acids). These are often referred to as fatty acids. As used herein the term "fatty" includes both even and odd number of carbon atoms in alkyl acids which may be linear or branched. Also included are C8-C22 mono- or polyunsaturated fatty acids. Examples include oleic, linoleic, linolenic, and arachidonic acids. For UV stability, preferably the alkyl carboxylate is saturated. Also included within this class are esters of these carboxylic acids with hydroxyfunctional alkyl acids (alkyl carboxylate esters of carboxylic acids) such as lauroyl lactylate, capryloil lactylate or caproyl lactylate. The alkyl carboxylate ester carboxylic acids comprise a C6-C14 (in some embodiments, C8-C12) alkyl group. Most conveniently, these are formed by esterification of a C6-C14 saturated linear or branched alkylcarboxylic acid or a C8-C22 mono- or polyunsaturated fatty acid with a hydroxyfunctional alkyl carboxylic acid. A commercially available example of an alkyl carboxylate ester of an alkyl carboxylic acid is caproyl lactylate marketed under the trade designation "PATIONIC 122A" from RITA Corp., Crystal Lake, IL Another exemplary compound of this class is lauroyl lactylate. Singlet oxygen is a potent antimicrobial and may be generated in-situ by exposing a suitable photosensitizer to light of the appropriate wavelength. In one embodiment, the photosensitizer is titanium dioxide (e.g., the anatase form), which is applied to or incorporated in the external surface, which is illuminated with UV light (200-320 nm). The photosensitizer is preferably applied by any suitable means such as vacuum deposition. Other photosensitizers and application methods are described in U.S. Pat. No. 7,569,181 (Curry et al.), the disclosure of which is incorporated herein by reference.

In some embodiments, UV-C light guides described herein can be a hollow tube, pipe, or hollow planar shape, wherein the hollow space within the tube comprises a gas. In some embodiments, hollow tube UV-C light guides described herein comprise a polymeric layer at least 25 (in some embodiments, at least 50, 60, 70, 80, 90, or even at least 95) percent transmissive over at least 30 nm in a wavelength range from 180 to 280 (in some embodiments, 200 to 230 or 250 to 280) nm over at least a distance of 100 micrometers and visible light transparent UV-C reflecting layers (UV-C mirror) that are at least 50 (in some embodiments, at least 60, 70, 75, 80, 90, 95, or even at least 99) percent reflective over at least 30 nm ultraviolet C bandwidth in a wavelength range from 180 to 280 (in some embodiments, 200 to 230 or 250 to 280) nanometers over an incident light angle of 0 to 90 degrees and that are at least 25 percent transmissive of visible light over at least 30 nm bandwidth in a wavelength range of 400 to 800 nm over an incident light angle of 0 to 90 degrees, rolled into a hollow tube.

In some embodiments, UV-C light guides described herein can be a hollow tube, pipe, or hollow planar shape, wherein the hollow space within the tube comprises a gas. In some embodiments, hollow tube UV-C light guides described herein comprise a polymeric layer at least 25 (in some embodiments, at least 50, 60, 70, 80, 90, or even at least 95) percent transmissive over at least 30 nm in a wavelength range from 180 to 280 (in some embodiments, 200 to 230 or 250 to 280) nm over at least a distance of 100 micrometers and visible light transparent UV-C reflecting layers (UV-C mirror) that are at least 50 (in some embodiments, at least 60, 70, 75, 80, 90, 95, or even at least 99) percent reflective over at least 30 nm ultraviolet C bandwidth in a wavelength range from 180 to 280 (in some embodiments, 200 to 230 or 250 to 280) nanometers over an incident light angle of 0 to 90 degrees and that are at least 25 percent transmissive of visible light over at least 30 nm bandwidth in a wavelength range of 400 to 800 nm over an incident light angle of 0 to 90 degrees, incorporated into an air disinfection device.

In some embodiments, hollow tube UV-C light guides described herein comprise a polymeric layer at least 25 (in some embodiments, at least 50, 60, 70, 80, 90, or even at least 95) percent transmissive over at least 30 nm in a wavelength range from 180 to 280 (in some embodiments, 200 to 230 or 250 to 280) nm over at least a distance of 100 micrometers on the first surface of visible light transparent UV-C reflecting layers (UV-C mirror) that are at least 50 (in some embodiments, at least 60, 70, 75, 80, 90, 95, or even at least 99) percent reflective over at least 30 nm ultraviolet C bandwidth in a wavelength range of 180 to 280 (in some embodiments, 200 to 230 or 250 to 280) nanometers over an incident light angle of 0 to 90 degrees and that are at least 25 percent transmissive of visible light over at least 30 nm in a wavelength range of 400 to 800 nm over an incident light angle of 0 to 90 degrees, and a second polymer layer on the second surface of the UV-C reflecting layers that are at least 25 (in some embodiments, at least 50, 60, 70, 80, 90, or even at least 95) percent transmissive over at least 30 nm bandwidth in a wavelength range from 180 to 280 (in some embodiments, 200 to 230 or 250 to 280) nm over at least a distance of 100 micrometers rolled into a hollow tube.

In some embodiments, UV-C light guides describe herein can be a hollow tube, pipe, or hollow planar shape, wherein the hollow space within comprises a liquid. In some embodiments, hollow tube UV-C light guides described herein comprise a polymeric layer at least 25 (in some embodiments, at least 50, 60, 70, 80, 90, or even at least 95) percent transmissive over at least 30 nm bandwidth in a wavelength range from 180 to 280 (in some embodiments, 200 to 230 or 250 to 280) nm over at least a distance of 100 micrometers and visible light transparent UV-C reflecting layers (UV-C mirror) that are at least 50 (in some embodiments, at least 60, 70, 75, 80, 90, 95, or even at least 99) percent reflective over at least 30 nm ultraviolet C bandwidth in a wavelength range from 180 to 280 (in some embodiments, 200 to 230 or 250 to 280) nanometers over an incident light angle of 0 to 90 degrees and that are at least 25 percent transmissive of visible light over at least 30 nm bandwidth in a wavelength range of 400 to 800 nm over an incident light angle of 0 to 90 degrees incorporated into a water disinfection device.

In some embodiments, light guides described herein are in the shape of a tube or a cone and are incorporated into a UV water treatment module. In general, UV treatment cartridges have an exterior housing having a first exterior end, a second exterior end, and an exterior sidewall connecting the first exterior end and the second exterior end. A cartridge inlet and a cartridge outlet are located on the exterior housing. A UV treatment module is located inside of the exterior housing. The UV treatment module includes an interior housing having a module first end, a module second end, and a module sidewall connecting the module first end and the module second end and enclosing a UV treatment chamber. The UV-C light guide, in the shape of a cylinder or cone, can be used as the module sidewall connecting the module first end and module second end of the UV treatment chamber. Additional details of UV fluid treatment cartridges can be found, for example, in PCT Pub. No. PCT/US2017/048859, published Mar. 15, 2018.

UV-C light sources for illuminating UV-C light guides described herein include UV-C LEDs and UV-C LED arrays, such as those available from Phoseon Technology, Hillsboro, OR; Irtronix Inc., Torrance, CA; and Crystal IS, Green Island, NY UV-C lights sources are also available, for example, from Far-UV Sterilray, Somersworth, NH, and Atlantic Ultraviolet Corporation, Hauppauge, NY Referring to FIG. 1, exemplary UV-C light guide described herein 10 is shown. UV-C light guide 10 comprises UV-C transparent protective layer 11 over UV-C reflective layers comprising first optical layers 12A, 12B, 12M, second optical layers 13A, 13B, 13M, UV-C transparent solid light guide layer 14, over optional UV-C reflective layers comprising optional third optical layers 15C, 15D, 15N, optional fourth optical layers 16C, 16D, 16N, optional UV-C transparent protective layer 17, and optional adhesive 18.

Figure 2:
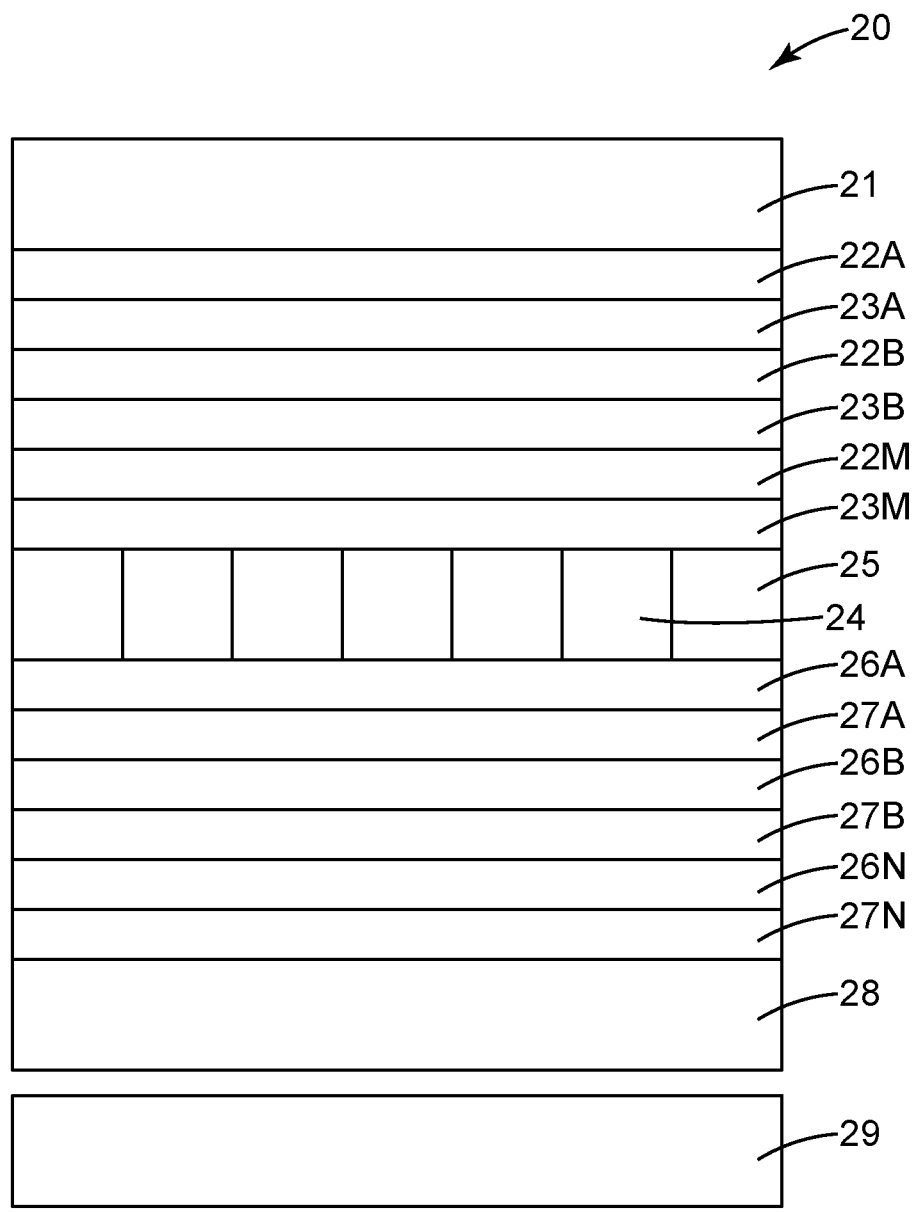
FIG. 2 is an exemplary hollow UV-C light guide described herein comprising at least one transparent UV-C mirror on a surface.

Referring to FIG. 2, exemplary UV-C light guide described herein 20 is shown. UV-C light guide 20 comprises UV-C transparent protective layer 21 over UV-C reflective layers comprising first optical layers 22A, 22B, 22M, second optical layers 23A, 23B, 23M, at least one air gap 24, at least one UV-C transparent spacer material 25, optional third optical layers 26A, 26B, 26N, optional fourth optical layers 27A, 27B, 27N, optional UV-C transparent protective layer 28, and optional adhesive layer 29.

Figure 3:
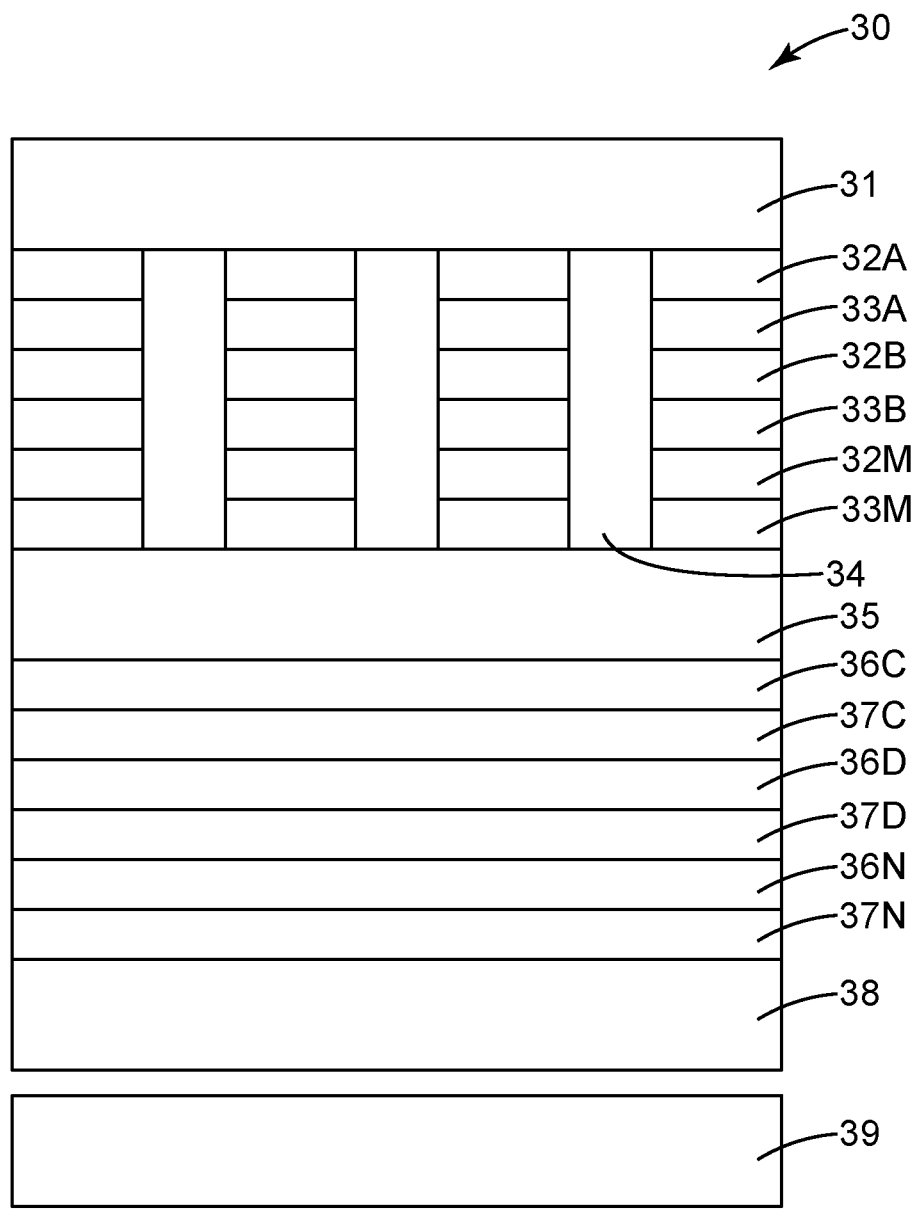
FIG. 3 is an exemplary solid UV-C light guide described herein comprising a discontinuous transparent UV-C mirror.

Referring to FIG. 3, exemplary UV-C light guide described herein 30 is shown. UV-C light guide 30 comprises UV-C transparent protective layer 31, over discontinuous UV-C reflective layers comprising first discontinuous optical layers 32A, 32B, 32M, second discontinuous optical layers 33A, 33B, 33M, at least one area with no UV-C reflective layers 34, a UV-C transparent solid light guide layer 35, over optional UV-C reflective layers comprising optional third optical layers 36C, 35D, 35N, optional fourth optical layers 37C, 37D, 37N, optional UV-C transparent protective layer 38, and optional adhesive 39.

Exemplary Embodiments

1A. A light guide comprising a polymeric layer at least 25 (in some embodiments, at least 50, 60, 70, 80, 90, or even at least 95) percent transmissive over at least 30 nm in a wavelength range from 180 to 280 (in some embodiments, 200 to 230 or 250 to 280) nm over at least a distance of 100 micrometers and visible light transparent UV-C reflecting layers (UV-C mirror) that are at least 50 (in some embodiments, at least 60, 70, 75, 80, 90, 95, or even at least 99) percent reflective over at least 30 nm in a wavelength range from 180 to 280 (in some embodiments, 200 to 230 or 250 to 280) nanometers over an incident light angle of 0 to 90 degrees and that are at least 25 percent transmissive of visible light over at least 30 nm in a wavelength range of 400 to 800 nm over an incident light angle of 0 to 90 degrees.

2A. The light guide of Exemplary Embodiment 1A further comprising a fluid (e.g., a liquid (e.g., an index matching fluid) or gas (e.g., air)) gap disposed between the polymeric layer and the reflecting layer.

3A. The light guide of Exemplary Embodiment 1A, wherein the fluid gap disposed between the polymeric layer and the reflecting layer has a thickness of at least 10, 100, or even 500 (in some embodiments, in a range from 10 to 1, 100 to 1000, or even 200 to 500) nanometers.

4A. The light guide of Exemplary Embodiment 1A further comprising porous material (e.g., nanosilica, microvoided polymer, and nano-voided polymer) gap disposed between the polymeric layer and the reflecting layer.

5A. The light guide of any preceding A Exemplary Embodiment, wherein the polymeric layer comprises at least one of fluoropolymers, polyolefin copolymers, cyclic olefin copolymers, or cyclic olefin block copolymers.

6A. The light guide of any preceding A Exemplary Embodiment, wherein the polymeric layer comprises fluoropolymer copolymers (e.g., fluoroethylenepolypropylene copolymer (FEP), perfluoroalkoxy (PFA), copolymer of tetrafluoroethylene, hexafluoropropylene, and vinylidene fluoride).

7A. The light guide of any preceding A Exemplary Embodiment, wherein the polymeric layer has first and second opposed major surfaces, and wherein at least one of the first or second major surface of the polymeric layer has a structured surface.

8A. The light guide of any preceding A Exemplary Embodiment, wherein the polymeric layer has a thickness of at least 5, 10, 50, 100, 500, 1000, 1500, 2000, 2500, or even at least 5000 (in some embodiments, in a range from 5 to 5000, 50 to 5000, 100 to 5000, 10 to 2500, 25 to 2500, 100 to 2500, or even 100 to 2000) micrometers.

9A. The light guide of any preceding A Exemplary Embodiment, wherein the reflecting layer has a thickness of at least 20, 30 or even at least 40 (in some embodiments, in a range from 10 to 70, 20 to 60, or even 30 to 60) nanometers.

10A. The light guide of any preceding A Exemplary Embodiment having a thickness of at least 10, 25, 50, 100, 500, 1000, 1500, 2000, 2500, or even at least 5000 (in some embodiments, in a range from 10 to 5000, 25 to 5000, 100 to 5000, 10 to 2500, 25 to 2500, 100 to 2500, or even 100 to 2000) micrometers.

11A. The light guide of any preceding A Exemplary Embodiment, wherein the reflecting layer is a dielectric mirror comprising alternating inorganic and organic layers, wherein the inorganic layers have a refractive index greater than 1.6, and wherein the organic layers have a refractive index less than 1.57.

12A. The light guide of any preceding A Exemplary Embodiment, wherein the reflecting layer is a dielectric mirror comprising polyolefin copolymer layers having a refractive index greater than 1.46, and fluoropolymer layers having a refractive index less than 1.42.

13A. The light guide of any of Exemplary Embodiments 1A to 8A, wherein the reflecting layer is diffuse particle mirror.

14A. The light guide of any preceding A Exemplary Embodiment, wherein the transparent mirror comprises inorganic layers and wherein the at least first optical layer comprises at least one of titania, zirconia, zirconium oxynitride, hafnia, or alumina, and wherein the second optical layer comprises at least one of silica, aluminum fluoride, or magnesium fluoride.

15A. The light guide of any preceding A Exemplary Embodiment, wherein the transparent mirror comprises polymeric layers and wherein the second optical layer comprises at least one of a copolymer comprising tetrafluoroethylene, hexafluoropropylene, and vinylidene fluoride, a copolymer comprising tetrafluoro-ethylene and hexafluoropropylene, or perfluoroalkoxy alkane.

16A. The light guide of any preceding A Exemplary Embodiment having first and second opposed sides, further comprising UV-C light sources (e.g., LED) embedded on at least side edge of the light guide, wherein the UV-C light sources are position such that when energized, provide UCV light within the light guide.

17A. The light guide of any of Exemplary Embodiments 1A to 15A further comprising an array of UV-C light sources (e.g., LED) embedded in the polymer layer facing away from the reflecting layers.

18A. The light guide of any preceding A Exemplary Embodiment further comprising adhesive, wherein the polymeric layer and the reflecting layer each have first and second opposed major surfaces, wherein the second major surface of the polymeric layer is adjacent to the first major surface of the reflecting layer, and wherein the adhesive is disposed on the second major surface of the reflecting layer.

19A. The light guide of Exemplary Embodiment 18A further comprising a removable liner on the adhesive layer.

20A. The light guide of any preceding A Exemplary Embodiment in the shape of a tube.

21A. The light guide of any preceding A Exemplary Embodiment in the shape of a rod.

22A. The light guide of any preceding A Exemplary Embodiment, wherein the light guide can be wrapped around a 1 cm diameter rod without breaking.

23A. The light guide of any preceding A Exemplary Embodiment further comprising anti-microbial additives.

24A. The light guide of any preceding A Exemplary Embodiment further comprising a wetting agent.

1B. A water purification device comprising a light guide of any preceding A Exemplary Embodiment.

1C. An air purification device comprising a light guide of any preceding A Exemplary Embodiment.

1D. An article comprising first and second light guides independently selected from any preceding A Exemplary Embodiment, wherein in the first and second light guides are positioned to be opposed to each other to have a fluid gap therebetween, separating their respective visible light transparent UV-C reflecting layers.

1E. An article comprising first and second light guides independently selected from any preceding A Exemplary Embodiment, wherein in the first and second light guides are positioned to be opposed to each other to have a fluid gap therebetween, separating their respective visible light transparent UV-C reflecting layers, and further comprising a solid polymer layer in the gap.

1F. The light guide of any A Exemplary Embodiment, wherein the polymeric layer and the reflecting layer each have first and second opposed major surfaces, wherein the second major surface of the polymeric layer is adjacent to the first major surface of the reflecting layer, and wherein the second major surface of the reflecting layer is attached to a substrate.

Advantages and embodiments of this invention are further illustrated by the following examples, but the particular materials and amounts thereof recited in these examples, as well as other conditions and details, should not be construed to unduly limit this invention. All parts and percentages are by weight unless otherwise indicated.

EXAMPLES

UV-C Service Life Test

UV-C service life was determined with an enclosure made of aluminum having a germicidal fixture (obtained under the trade designation "118V RRD-30-8S" from Atlantic Ultraviolet Corporation, Hauppauge, NY). The fixture contained eight high output instant start 254 nm UV-C lamps. Compressed air was run across the length of the lamps at a pressure of 124 kPa (18 psi) to maintain a constant temperature and minimize temperature-induced loss of lamp output intensity. Test samples were mounted onto aluminum slides containing a window of appropriate size to conduct absorbance measurements using a spectrophotometer (obtained under the trade designation "SHIMADZU 2550 UV-VIS" from Shimadzu, Kyoto, Japan). Continuous light exposures were conducted for discrete time intervals, with removal for absorbance measurement every 100 hours, and placed back into the exposure chamber. Samples were placed within the test chamber at a controlled height from and distance along the lamps throughout the duration of experiments. A UV radiometer (obtained under the trade designation "UVPAD" from OPSYTECH Corporation, Makati City, Philippines) was placed within the chamber in line with test samples to gather UV-C irradiance and dosage data every 100 hours throughout the exposure process.

The UV-C light source was a UV-C 275 nm LED light source (obtained under the trade designation "FIREJET FJ200 300×20AC275-3W" from Phoseon Technology, Hillsboro, OR). The emitter window was 300 mm×20 mm and the LEDs had an output wavelength of 278 nm with a full width at half max of 11 nm. Peak irradiance measured at the emitter window was 3 W/cm$^2$. UV-C intensity measurements were made with spectroradiometer (obtained as Model ILT950UV from International Light Technologies Inc., Peabody, MA) with a solid core fiber (obtained under the trade designation "FFO600SC" from International Light Technologies Inc.) and either a low profile right angle cosine adapter (obtained under the trade designation "RAA4" from International Light Technologies Inc.) or a mini cosine correcting diffuser (obtained under the trade designation "W5E" from International Light Technologies Inc.).

Example 1

Figure 4:
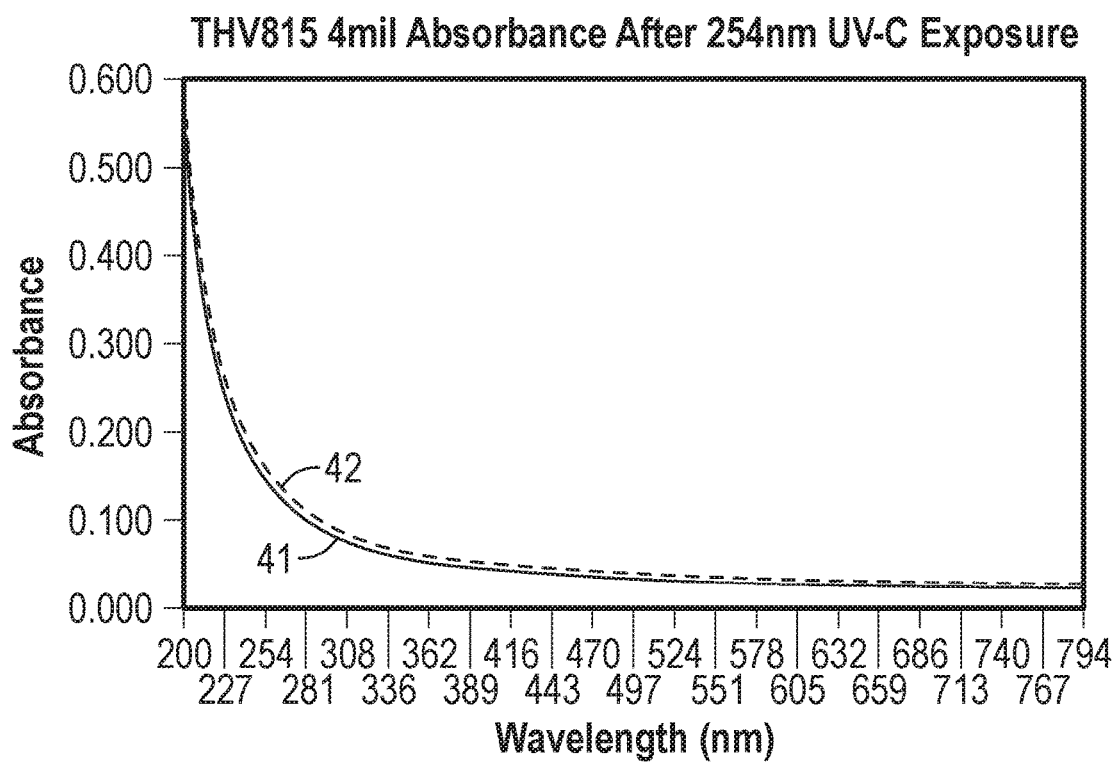
FIG. 4 is a graph of measured absorbance spectra of exemplary fluoropolymer film described herein.

Fluoropolymer (available under the trade designation "THV815GZ" from Dyneon, Oakdale, MN) was extruded with a 40 mm twin screw extruder and a flat film extrusion die onto a film casting wheel chilled to 21° C. (70° F.) to create a 100-micrometer thick fluoropolymer ("THV815GZ") film. Film absorbance spectra of the fluoropolymer ("THV815GZ") film was measured per the UV-C service life test and initial spectra 41 is shown in FIG. 4. The fluoropolymer ("THV815GZ") film was then exposed to 254 nm light as described in UV-C Service Life Test Method for 1588 hours for a total dose of 105,108,800 mj/cm$^2$. After exposure, the fluoropolymer ("THV815GZ") film absorbance spectra was again measured per the UV-C service life test and the absorbance spectra 42 is shown in FIG. 4.

Example 2

A UV-C mirror was made by vapor coating an inorganic optical stack having first optical layers comprising HfO$_2$ and second optical layers comprising SiO$_2$, onto 100 micrometers (4 mil) thick fluoropolymer film (obtained under the trade designation "NOWOFLON THV815" from NOWOFOL Kunststoffprodukte GmbH & Co., Siegsdorf, Germany). More specifically, a thin film stack comprised of alternating layers of HfO$_2$ and SiO$_2$ and designed to have peak reflectance at 280 nm began by coating layer 1 HfO$_2$ at 30.00 nm was coated. In electron beam deposition, a four-hearth evaporation source was used. Each hearth was cone-shaped and 17 cm$^3$ volume of HfO$_2$ chunks filled it. The magnetically deflected high voltage electron beam was raster scanned over the material surface as filament current of the beam was steadily, in a pre-programmed fashion, increased. Upon completion of the pre-programmed step, the HfO$_2$ surface was heated to evaporation temperature, about 2500° C., and a source shutter opened, the HfO$_2$ vapor flux emerging from the source in a cosine-shaped distribution and condensing upon the substrate material above the source. For enhancement of coating uniformity, the substrate holders rotated during deposition. Upon reaching the prescribed coating thickness (30.00 nm) the filament current shut off; the shutter closed and the HfO$_2$ material cooled. For second layer, the evaporation source was then rotated to a hearth containing chunks of SiO$_2$ and a similar pre-programmed heating process begins. Here, the SiO$_2$ surface temperature was about 950° C. when the source shutter opened and, upon reaching the prescribed coating thickness (45.02 nm), the filament current shut off; the shutter closed and the HfO$_2$ material cooled. This step-wise process was continued, layer by layer, until a total number of 13 layers was reached. Resulting peak reflectance was measured with the spectrophotometer ("SHIMADZU 2550 UV-VIS") and found to be 79% at 280 nm with greater than 70% reflectance over a wavelength range from 260 nm to 300 nm. Visible light transmission was also measured with the spectrophotometer ("SHIMADZU 2550 UV-VIS") to be greater than 85% over a wavelength range of 400 nm to 800 nm. Fluoropolymer (obtained under the trade designation "THV221GZ" from Dyneon, Oakdale, MN) was extruded with a 40 mm twin screw extruder and a flat film extrusion die onto a film casting wheel chilled to 21° C. (70° F.) to create a 100-micrometer thick fluoropolymer ("THV221") film. Two 75-micrometers×75-micrometers pieces of the UV-C mirror films made as described above were heat laminated to a 300-micrometer thick layer of fluoropolymer ("THV221") film using a hot press at 135° C. to form a UV-C light guide as shown in FIG. 1. The UV-C light guide was attached to a UV-C 275 nm LED light source ("FIREJET FJ200 300×20AC275-3W") with aluminum tape to prevent escape of UV-C light at the entrance to the light guide. UV-C measurements were made at the surface and end of the UV-C light guide with a spectroradiometer ("ILT950UV") and with a low profile right angle cosine adapter ("RAA4"). UV-C intensity at the surface of the UV-C light guide at a distance of 1 inch (2.5 cm) from the light source was 14 microwatts/cm$^2$. UV-C intensity at the end of the UV-C light guide at a distance of 2-inches (5.1 cm) from the light source was 363 microwatts/cm$^2$.

Example 3

A UV-C light guide was as described for Example 2, except the 300-micrometer thick layer of fluoropolymer ("THV221") film was cut into 1 cm wide strips separated by 1 cm gaps effectively leaving 1 cm wide air gaps by 300 micrometers height as shown in FIG. 2. The UV-C light guide was attached to a UV-C 275 nm LED light source ("FIREJET FJ200 300×20AC275-3W") with aluminum tape to prevent escape of UV-C light at the entrance to the light guide. UV-C measurements were made at the surface of the air gaps and end of the air gap of the hollow UV-C light guide with the spectroradiometer ("ILT950UV") with the low profile right angle cosine adapter ("RAA4"). UV-C intensity at the surface of the hollow UV-C light guide at a distance of 1-inch (2.5 cm) from the light source was 95 microwatts/cm$^2$. UV-C intensity at the end of the hollow UV-C light guide at a distance of 2-inches (5.1 cm) from the light source was 480 microwatts/cm$^2$.

Example 4

A UV-C light guide was made as described for Example 3, except the 1 cm wide strips of fluoropolymer ("THV221") were 3 mm thick. The UV-C light guide was attached to a UV-C 275 nm LED light source ("PHOSEON") with aluminum tape to prevent escape of UV-C light at the entrance to the light guide. UV-C measurements were made at the surface of the air gaps and end of the air gap of the hollow UV-C light guide with the spectroradiometer ("ILT950UV") with the mini cosine correcting diffuser ("W5E"). UV-C intensity at the surface of the hollow UV-C light guide at a distance of 1-inch (2.5 cm) from the light source was 1135 microwatts/cm². UV-C intensity at the end of the hollow UV-C light guide at a distance of 2-inches (5.1 cm) from the light source was 1898 microwatts/cm².

Example 5

Figure 8:
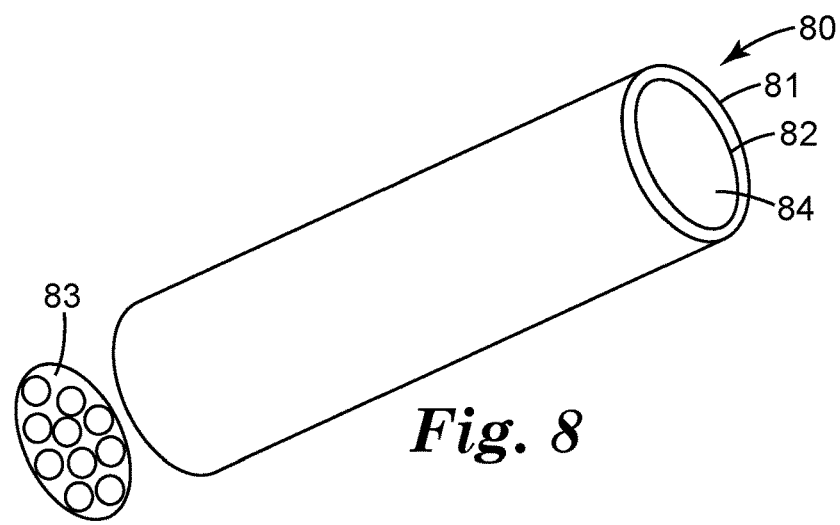
FIG. 8 is an exemplary hollow light guide described herein in the shape of a tube.

A UV-C mirror was made by vapor coating an inorganic optical stack having first optical layers comprising $HfO_2$ and second optical layers comprising $SiO_2$ onto 100 micrometers (4 mil) thick fluoropolymer film ("NOWOFLON THV815"). More specifically, a thin film stack comprised of alternating layers of $HfO_2$ and $SiO_2$ and designed to have peak reflectance at 280 nm were made by coating layer 1 $HfO_2$ at 30.00 nm. In electron beam deposition, a four-hearth evaporation source was used. Each hearth was cone-shaped and 17 cm³ volume of $HfO_2$ chunks filled it. The magnetically deflected high voltage electron beam was raster scanned over the material surface as filament current of the beam was steadily, in a pre-programmed fashion, increased. Upon completion of the pre-programmed step, the $HfO_2$ surface was heated to evaporation temperature, about 2500° C., and a source shutter opened, the $HfO_2$ vapor flux emerging from the source in a cosine-shaped distribution and condensing upon the substrate material above the source. For enhancement of coating uniformity, the substrate holders rotated during deposition. Upon reaching the prescribed coating thickness (30.00 nm) the filament current shut off; the shutter closed and the $HfO_2$ material cooled. For second layer, the evaporation source was then rotated to a hearth containing chunks of $SiO_2$ and a pre-programmed heating process was used. Here, the $SiO_2$ surface temperature was about 950° C. when the source shutter opened and, upon reaching the prescribed coating thickness (45.02 nm), the filament current shut off; the shutter closed and the $HfO_2$ material cooled. This step-wise process was continued, layer by layer, until a total number of 13 layers was reached. Resulting peak reflectance was measured with a spectrophotometer ("SHIMADZU 2550 UV-VIS") and found to be 89% at 280 nm. Hollow UV-C light guide 80 is shown in FIG. 8. UV-C transparent layer 81 and UV-C reflecting layers 82 were then rolled into a 3.175 cm diameter hollow tube by 25.4 cm long. Hollow UV-C light guide 80 was attached to a 278 nm UVC LED source ("FIREJET FJ200 300×20AC275-3W") with aluminum tape to prevent escape of UV-C light at the entrance. UV-C measurements were made at the surface and end of the UV-C light guide with the spectroradiometer ("ILT950UV") with the mini cosine correcting diffuser ("W5E"). UV-C intensity at the outer surface of the UV-C light guide at a distance of 9-inches (22.86 cm) from the light source was 4706 microwatts/cm². UV-C intensity at opening 84 of the UV-C light guide 80 at a distance of 10-inches (25.4 cm) from the light source was 136,363 microwatts/cm². UV-C intensity without the UV-C light guide at a distance of 10-inches (25.4 cm) from the light source was 3572 microwatts/cm².

Example 6

A UV-C light guide was made as described for Example 2, except 10 micrometer strips of the UV-C reflective layers were skived away with a razor blade with 1 cm spacing and perpendicular from the UV-C 275 nm LED light source ("FIREJET FJ200 300×20AC275-3W"). UV-C intensity measured with the spectroradiometer ("ILT950UV") with the mini cosine correcting diffuse ("W5E") at the surface of the solid UV-C light guide at a distance of 1 cm from the light source was 9217 microwatts/cm² and at distance of 2 cm from the light source was 121.5 microwatts/cm². UV-C intensity at the end of the solid UV-C light guide at a distance of 5.1 cm from the light source was 277.5 microwatts/cm².

Prophetic Example I

Figure 5:
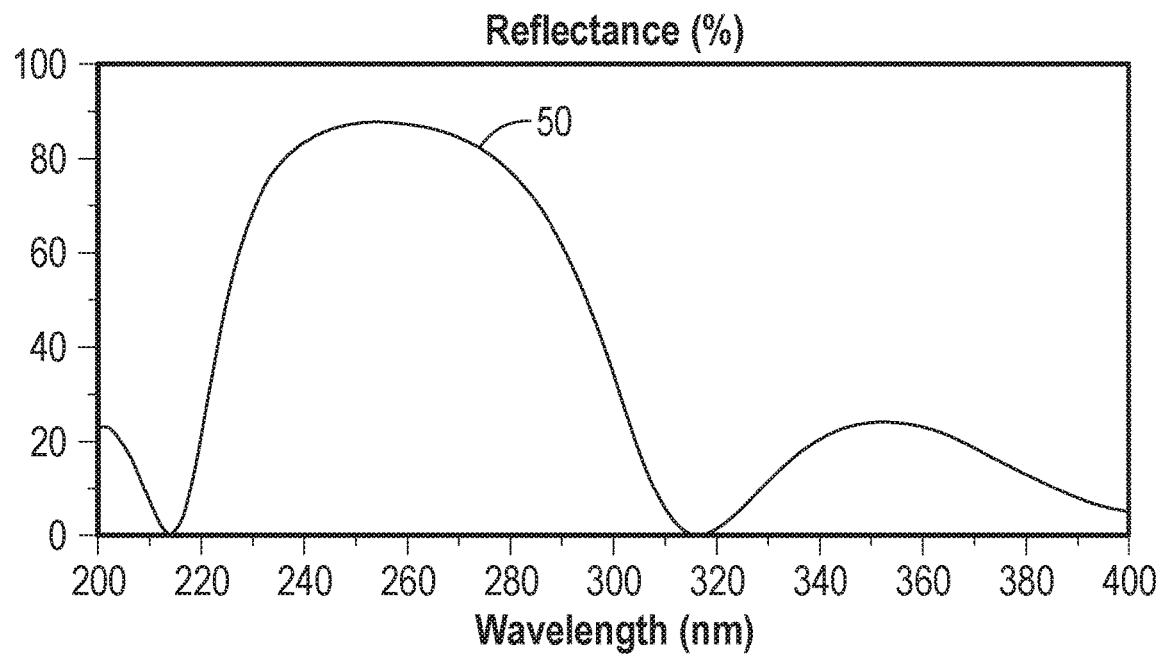
FIG. 5 is a graph of modeled reflection spectra of exemplary multilayer optical film described herein.

The 4×4 matrix method using the Berreman algorithm was used for modeling the spectra of constructive and destructive interference generated from layer interfaces of materials having different refractive indices. The Berreman 4×4 matrix methodology is described in the Journal of the Optical Society of America (Volume 62, Number 4, April 1972) and the Journal of Applied Physics (Volume 85, Number 6, March 1999), the disclosures of which are incorporated herein by reference. Input parameters for this optical model were individual layer refractive indices, layer thicknesses, number of layers, and reflection bandwidth including a left band edge and a right band edge. The Berreman methodology calculated the percent light reflected at each layer interface and the percent light transmitted at each layer interface and outputs a reflection spectra and transmission spectra. The Berreman methodology was used to calculate % Reflectance spectra 50 shown in FIG. 5 of UV-C multilayer optical film having 10 alternating optical layers of $HfO_2$ high refractive index layers and $SiO_2$ low refractive index layers for a peak reflectance target of 254 nm.

Prophetic Example II

Figure 6:
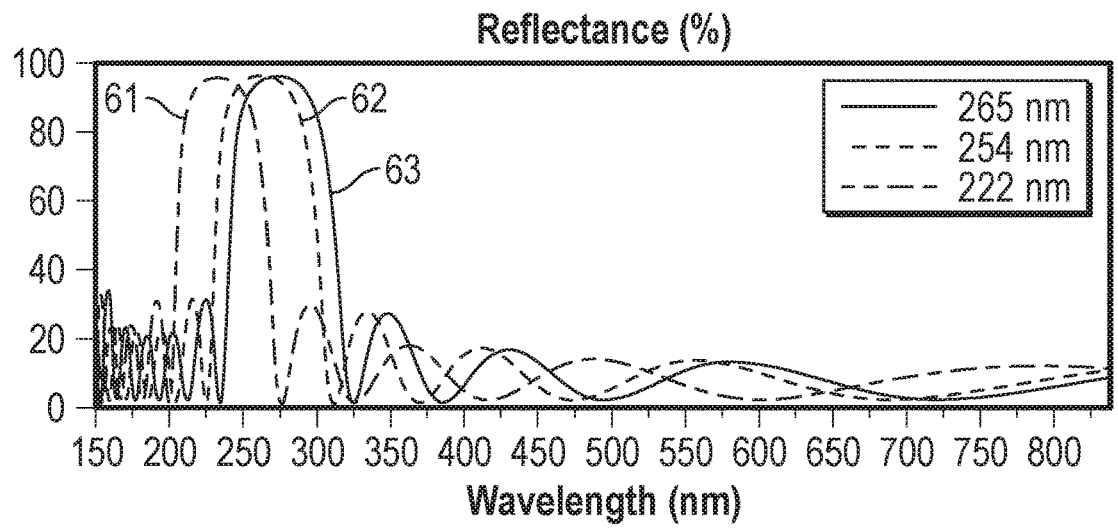
FIG. 6 is a graph of modeled reflection spectra of three different exemplary multilayer optical films described herein.

The Berreman methodology described in Prophetic Example I was used to calculate % Reflectance spectra 61 shown in FIG. 6 for multilayer optical film with 11 alternating optical layers of $HfO_2$ high refractive index layers and $SiO_2$ low refractive index layers for reflectance spectra median target of 222 nm. % Reflectance spectra 62 was calculated for the same multilayer optical layers, but for a reflectance spectra median target of 254 nm. % Reflectance spectra 63 was calculated for the same multilayer optical layers, but for a reflectance spectra median target of 265 nm. % Reflectance spectra 64 was calculated for the same multilayer optical layers, but for a reflectance spectra median target of 275 nm.

Prophetic Example III

Figure 7:
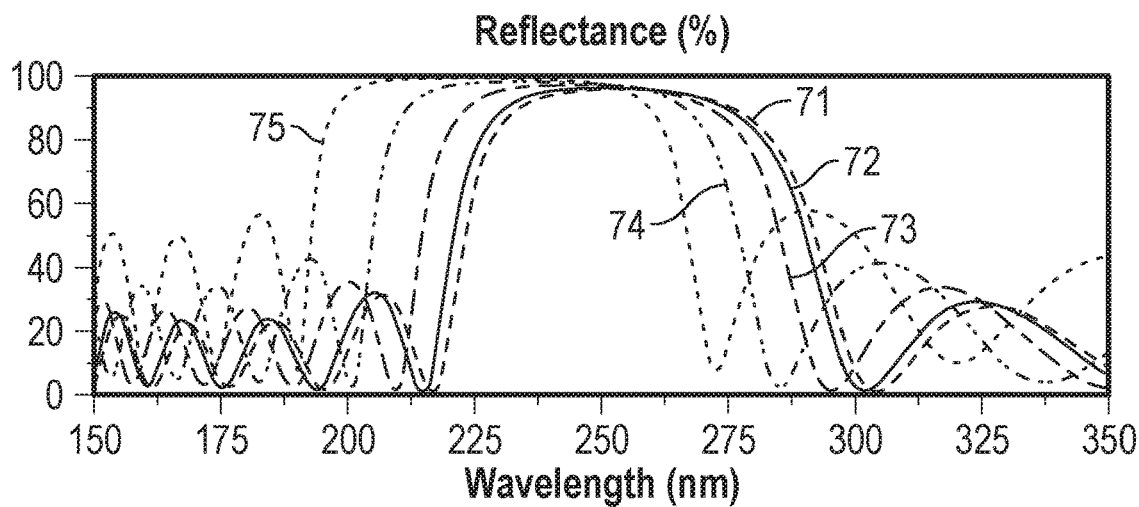
FIG. 7 is a graph of modeled reflection spectra of exemplary multilayer optical film showing shift in reflection spectra with changing incident light angle as described herein.

The Berreman methodology described in Prophetic Example I was used to calculate % Reflectance spectra 71 shown in FIG. 7 for a multilayer optical film with 14 alternating optical layers of ZrON high refractive index layers and $SiO_2$ low refractive index layers for a median reflectance target of 254 nm at normal incident light angle (0°). % Reflectance spectra 72 was calculated for the same multilayer optical film, but for an incident light angle of 10°. % Reflectance spectra 73 was calculated for the same multilayer optical film, but for an incident light angle of 20°. % Reflectance spectra 74 was calculated for the same multilayer optical film, but for an incident light angle of 30°. % Reflectance spectra 75 was calculated for the same multilayer optical film, but for an incident light angle of 40°.

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A light guide comprising
   (A) a polymeric layer at least 25 percent transmissive over at least 30 nm bandwidth in a wavelength range from 180 to 280 nanometers over at least a distance of 100 micrometers and
   (B) a plurality of visible light transparent UV-C reflecting layers that is
      (i) at least 50 percent reflective over at least 30 nanometers in a wavelength range from 180 to 280 nanometers over an incident light angle of 0 to 90 degrees and (ii) at least 25 percent transmissive of visible light over at least 30 nm in a wavelength range of 400 to 800 nm over an incident light angle of 0 to 90 degrees,
   wherein each visible light transparent UV-C reflecting layer is a dielectric mirror comprising a first optical layer and an adjacent second optical layer.

2. The light guide of claim 1 further comprising a fluid gap disposed between the polymeric layer and the plurality of visible light transparent UV-C reflecting layers.

3. The light guide of claim 1, wherein the polymeric layer comprises at least one of fluoropolymers, polyolefin copolymer, cyclic olefin copolymers, or cyclic olefin block copolymers.

4. The light guide of claim 1, wherein the polymeric layer has first and second opposed major surfaces, and wherein at least one of the first or second major surface of the polymeric layer has a structured surface.

5. The light guide of claim 1, wherein the visible light transparent UV-C reflecting layers comprise inorganic layers and wherein at least first optical layer comprises at least one of titania, zirconia, zirconium oxynitride, hafnia, or alumina, and wherein at least one second optical layer comprises at least one of silica, aluminum fluoride, or magnesium fluoride.

6. The light guide of claim 1, wherein the visible light transparent UV-C reflecting layers comprise polymeric layers and wherein at least one second optical layer comprises at least one of a copolymer comprising tetrafluoroethylene, hexafluoropropylene, and vinylidene fluoride, a copolymer comprising tetrafluoro-ethylene and hexafluoropropylene, or perfluoroalkoxy alkane.

7. The light guide of claim 1 having first and second opposed sides, further comprising UV-C light sources embedded on at least side edge of the light guide, wherein the UV-C light sources are position such that when energized provide UC-V light within the light guide.

8. The light guide of claim 1, further comprising an array of UV-C light sources embedded in the polymer layer facing away from the reflecting layers.

9. The light guide of claim 1, comprising two opposing light guides described in claim 1, wherein a fluid gap separates the opposing visible light transparent UV-C reflecting layers.

10. The light guide of claim 1, comprising two opposing light guides described in claim 1, wherein a solid polymer separates the opposing visible light transparent UV-C reflecting layers and the visible light transparent UV-C reflecting layers are adjacent to the solid polymer layer.

11. The light guide of claim 1 in the shape of a hollow tube, pipe, or cylinder.

12. The light guide of claim 1 where the light guide can be wrapped around a 1 cm diameter rod without breaking.

13. The light guide of claim 1 further comprising anti-microbial additives.

14. The light guide of claim 1, further comprising a wetting agent.

15. A water purification device comprising the light guide of claim 1.

* * * * *